(12) United States Patent
Betzig et al.

(10) Patent No.: US 8,629,413 B2
(45) Date of Patent: Jan. 14, 2014

(54) MICROSCOPY WITH ADAPTIVE OPTICS

(75) Inventors: Eric Betzig, Ashburn, VA (US); Na Ji, Ashburn, VA (US)

(73) Assignee: Howard Hughes Medical Institute, Ashburn, VA (US)

( * ) Notice: Subject to any disclaimer, the term of this patent is extended or adjusted under 35 U.S.C. 154(b) by 0 days.

(21) Appl. No.: 13/550,250

(22) Filed: Jul. 16, 2012

(65) Prior Publication Data

US 2013/0181143 A1 Jul. 18, 2013

Related U.S. Application Data

(63) Continuation of application No. PCT/US2012/046815, filed on Jul. 13, 2012.

(60) Provisional application No. 61/507,906, filed on Jul. 14, 2011.

(51) Int. Cl.
*G01N 21/64* (2006.01)

(52) U.S. Cl.
USPC ..................................... 250/459.1; 250/578.1

(58) Field of Classification Search
USPC ......... 250/461.1, 461.2, 459.1; 356/317, 318; 359/368, 385
See application file for complete search history.

(56) References Cited

U.S. PATENT DOCUMENTS

| | | | |
|---|---|---|---|
| 5,801,881 A * | 9/1998 | Lanni et al. | 359/386 |
| 6,483,641 B1 | 11/2002 | MacAulay | |
| 6,750,457 B2 * | 6/2004 | Heffelfinger et al. | 250/458.1 |
| 6,771,417 B1 | 8/2004 | Wolleschensky et al. | |
| 6,863,406 B2 * | 3/2005 | Grier et al. | 359/614 |
| 6,995,810 B2 | 2/2006 | Melton | |
| 7,079,262 B2 * | 7/2006 | Jones et al. | 356/630 |
| 7,095,556 B2 * | 8/2006 | Iketaki et al. | 359/385 |
| 7,180,661 B2 | 2/2007 | Sasaki | |
| 7,359,117 B2 | 4/2008 | Shimizu et al. | |
| 7,423,745 B2 | 9/2008 | Moribe et al. | |

(Continued)

FOREIGN PATENT DOCUMENTS

| | | |
|---|---|---|
| WO | WO 9731276 A1 * | 8/1997 |
| WO | 2011006106 A1 | 1/2011 |
| WO | 2013010151 A1 | 1/2013 |

OTHER PUBLICATIONS

Author: Meng Cui, Title: Parallel wavefront optimization method for focusing light through random scattering media, Date: Mar. 15, 2011, Publisher: Optics Letter, Edition: vol. 36, No. 6.*

(Continued)

*Primary Examiner* — David Porta
*Assistant Examiner* — Taeho Jo
(74) *Attorney, Agent, or Firm* — Brake Hughes Bellermann LLP

(57) ABSTRACT

A method of manipulating a focused light beam includes focusing a beam of excitation light with a lens to a focal spot within a sample, where a cross-section of the beam includes individual beamlets. Directions and/or relative phases of the individual beamlets of the excitation beam at a rear pupil of the lens are individually varied with a wavefront modulating element, and emission light emitted from the focal spot is detected while the directions or relative phases of individual beamlets are varied. The directions of individual beamlets are controlled to either maximize or minimize the emission light from the focal spot, and the relative phases of individual beamlets are controlled to increase the emission light from the focal spot.

69 Claims, 12 Drawing Sheets

(56) References Cited

U.S. PATENT DOCUMENTS

| | | | |
|---|---|---|---|
| 7,460,248 | B2 | 12/2008 | Kurtz et al. |
| 7,755,832 | B2 | 7/2010 | MacAulay |
| 8,217,992 | B2* | 7/2012 | Bewersdorf et al. ............ 348/47 |
| 2002/0154398 | A1 | 10/2002 | Wolleschensky et al. |
| 2003/0161038 | A1* | 8/2003 | Tobben et al. ................ 359/386 |
| 2004/0257529 | A1 | 12/2004 | Thomas |
| 2006/0058682 | A1* | 3/2006 | Miller et al. .................. 600/476 |
| 2007/0121201 | A1 | 5/2007 | Sander |
| 2007/0188856 | A1 | 8/2007 | MacAulay |
| 2007/0263226 | A1 | 11/2007 | Kurtz et al. |
| 2008/0316571 | A1 | 12/2008 | MacAulay |
| 2009/0046298 | A1* | 2/2009 | Betzig ........................... 356/521 |
| 2009/0137990 | A1 | 5/2009 | Sheinis |
| 2009/0316141 | A1* | 12/2009 | Feldkhun ...................... 356/217 |
| 2010/0102249 | A1* | 4/2010 | Akselrod et al. ........... 250/459.1 |
| 2010/0301232 | A1* | 12/2010 | Erlbacher et al. .......... 250/459.1 |
| 2011/0006231 | A1* | 1/2011 | Betzig et al. ............... 250/578.1 |
| 2011/0278442 | A1* | 11/2011 | Grier et al. .................... 250/251 |

OTHER PUBLICATIONS

Author: Meng Cui, Title: A high speed wavefront determination method based on spatial frequency modulations for focusing light through random scattering media, Date: Feb. 14, 2011, Publisher: Optical Society of America, Edition: vol. 19, No. 6.*

International Search Report and Written Opinion received for PCT Patent Application No. PCT/US2010/41582, mailed on Sep. 30, 2010, 17 pages.

Moreno-Barriusco, E., et al., "Laser Ray Tracing versus Hartmann-Shack sensor for measuring optical abberrations in the human eye", Journal of the Optical Society of America A, Optical Society of America, vol. 17 No. 06, Jun. 6, 2000, pp. 974-985.

Navarro, R., et al., "Laser Ray-Tracing Method for Optical Testing", Optics Letters, OSA, Optical Society of America, vol. 24 No. 14, Jul. 15, 1999, pp. 951-953.

Booth, J. M., "Adaptive optics in microscopy", Philosophical Transactions of the Royal Society: A Mathematical, Physical and Engineering Sciences, vol. 365, Issue 1861, Sep. 13, 2007, pp. 2829-2842.

Ji et al., "Adaptive optics via pupil segmentation for high-resolution imaging in biological tissues", Nature Methods vol. 7, 2009, pp. 141-147.

Vellekoop et al., "Focusing coherent light through opaque strongly scattering media", Optics Letters vol. 32 No. 16, 2007, pp. 2309-2311.

Wright et al., "Dynamic Closed-Loop System for Forcus Tracking Using A Spatial Light Modulator And A Deformable Membrane Mirror", Institute of Photonics, University of Strathclyde, 106 Rottenrow, Glasgow, G4-NW, Scotland, Optics Express 222, vol. 14, No. 1, Jan. 9, 2006, 7 Pages.

Webb et al., "Measurement of Ocular Local Wavefront Distortion with a Spatially Resolved Refractometer", Applied Optics, vol. 31, No. 19, Jul. 1, 1992, 9 pages.

Webb et al., "SSR (spatially resolved refactormeter): A Null-Seeking Aberrometer", Applied Optics, vol. 42, No. 4, Feb. 1, 2003, 9 Pages.

Leray, A., et al., "Enhanced Background Rejection in Thick Tissue with Differential-Aberration Two-Photon—Microscopy", Biophysical Journal, vol. 94, Feb. 2008, 10 Pages.

Lombardo et al., "New Methods and Techniques for Sensing the Wave Aberrations of Human Eyes", Clin Exp Optom; 92: 3, Dec. 24, 2009, pp. 176-186.

He et al., "Measurement of the Wave-front Aberration of the Eye by a Fast Psychophysical Procedure", vol. 15, No. 9, J. Opt. Soc. Am A., Sep. 1998, pp. 2449-2456.

Sebag et al., "High-resolution Imaging using Pupil Segmentation", vol. 7, No. 7, J. Opt.Soc. Am. A, Jul. 1990, 6 Pages.

Liu et al., "Dynamic Focusing with Radial Gratings for in VIVO High Resoluation Imaging", Proc. of SPIE vol. 6847 684718-1, Coherence Domain Optical Methods and Optical Coherence Tomography in Biomedicine XII, 2008, 8 Pages.

Kner et al., "Applying Adaptive Optics to Three-Dimensional Wide-Field Microscopy", 12 pages.

International Search Report and Written Opinion received for PCT Patent Application No. PCT/US2012/046815, mailed on Sep. 26, 2012, 8 pages.

Birch et al.,"Dynamic Complex Wave-Front Modulation with an Analog Spatial Light Modulator", Optical Society of America. Optics Letters, vol. 26, No. 12, Jun. 15, 2001, pp. 920-922.

Booth et al., "Methods for the Characterization of Deformable Membrane Mirrors", Optical Society of America, Applied Optics, vol. 44, No. 24, Aug. 20, 2005, pp. 5131-5139.

Hanser et al., "Phase-Retrieved Pupil Functions in Wide-Field Fluorescence Microscopy", The Royal Microscopical Society, Journal of Microscopy, vol. 216, Pt, Oct. 1, 2004, pp. 32-48.

Helmchen et al., "Deep Tissue Two-Photon Microscopy", Nature Publishing Group, Nature Methods, vol. 2, No. 12, Dec. 2005, pp. 932-940.

Schwertner et al., "Measurement of Specimen-Induced Aberrations of Biological Samples Using Phase Stepping Interferometry", The Royal Microscopical Society, Journal of Microscopy, vol. 213, Pt, Jan. 1, 2004, pp. 11-19.

Neil et al., "New Modal Wave-Front Sensor: A Theoretical Analysis", Optical Society of America, J. Opt. Soc. Am. A, vol. 17, No. 6, Jun. 2000, pp. 1098-1107.

Booth et al., "New Modal Wave-Front Sensor: Application to Adaptive Confocal Fluorescence Microscopy and Two-Photon Excitation Fluorescence Microscopy", Optical Society of America, J. Opt. Soc. Am. A, vol. 19, No. 10, Oct. 2002, pp. 2112-2120.

Schwertner et al., "Spherical Aberration Correction System Using an Adaptive Optics Deformable Mirror", Elsevier B.V. Science Direct, Optics Communications 263, 2006, pp. 147-151.

Vellekoop et al., "Phase Control Algorithms for Focusing Light Through Turbid Media", Elsevier B.V., Science Direct, Optics Communications 281, 2008, pp. 3071-3080.

Schwertner et al., "Characterizing Specimen Induced Aberrations for High NA Adaptive Optical Microscopy", Optical Society of America, Optics Express 6540, vol. 12, No. 26, Dec. 27, 2004, 13 Pages.

Debarre et al., "Image Based Adaptive Optics Through Optimisation of Low Spatial Frequencies", Optical Society of America, Optics Express 8176, vol. 15, No. 13, Jun. 25, 2007, 15 Pages.

Hanser et al., "Phase Retrieval for High-Numerical-Aperture Optical Systems", Optical Society of America, Optics Letters, vol. 28, No. 10, May 15, 2003, pp. 801-803.

Booth, Martin J., "Wavefront Sensorless Adaptive Optics for Large Aberrations", Optical Society of America, Optics Letters, vol. 32, No. 1, Jan. 1, 2007, pp. 5-7.

Botcherby, et al, "An Optical Technique for Remote Focusing in Microscopy", Optics Communications 281, 2008, pp. 880-887.

Booth et al., "Adaptive Aberration Correction in a Confocal Microscope", PNAS, vol. 99, No. 9, Apr. 30, 2002, pp. 5788-5792.

Schwiegerling et al., "Historical Development of the Shack-Hartmann Wavefront Sensor", 5 Pages.

Chen et al., "Focal Modulation Microscopy", Optical Society of America, Optics Express 18764, vol. 16, No. 23, Nov. 10, 2008, 6 Pages.

Vellekoop, Ivo Micha, "Controlling the Propagation of Light in Disordered Scattering Media", ISBN: 978-90-365-2663-0, Nov. 11, 1977, 144 Pages.

Cui, M., "Parallel Wavefront Optimization Method for Focusing Light through Random Scattering Media", Optics Letters, vol. 36, No. 6, Mar. 15, 2011, pp. 870-872.

Hardy, J. W., "Adaptive Optics for Astronomical Telescopes", Oxford University Press, Jul. 30, 1998, 448 Pages.

Helmbrecht et al., "MEMS DM Development at Iris AO Inc.", Inc. Proc. SPIE, vol. 7931 No. 1, 2011.

Non-Final Office Action for U.S. Appl. No. 12/833,767, mailed Oct. 5, 2012, 9 pages.

International Preliminary Report on Patentability received for PCT Patent Application No. PCT/US2010/41582, mailed on Jan. 19, 2012 , 10 Pages.

Tyson, R. K., "Principles of Adaptive Optics", San Diego, CA: Academic Press, Inc., Sep. 16, 2010, 299 Pages.

(56) References Cited

OTHER PUBLICATIONS

Ji, Na "Advances in the Speed and Resolution of Light Microscopy", Current Opinion in Neurobiology, www.sciencedirect.com, (2008), 12 pages.

Girkin, John M., et al., "Adaptive Optice for Deeper Imaging of Biological Samples", Current Opinion in Biotechnology, www.sciencedirect.com, (2998), 5 pages.

Final Office Action for U.S. Appl. No. 12/833,767, mailed May 16, 2013, 9 pages.

* cited by examiner

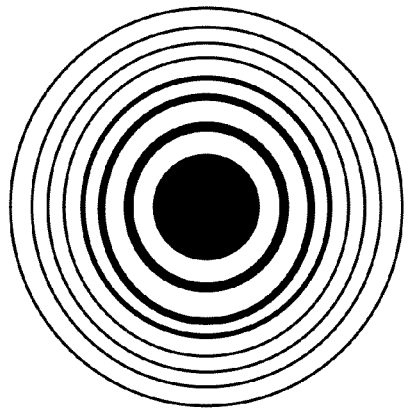
FIG 11A
A
FIG 11B
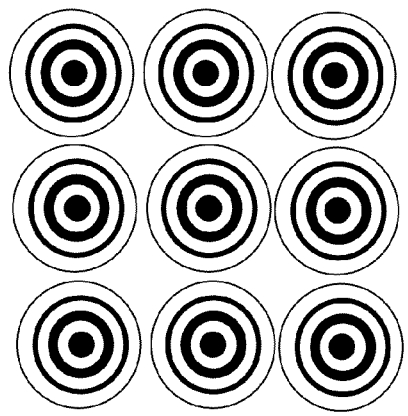
FIG. 11C
A    A    A
A    A    A
A    A    A
FIG. 11D

MICROSCOPY WITH ADAPTIVE OPTICS

CROSS-REFERENCE TO RELATED APPLICATIONS

This application is a continuation of International Patent Application, Serial No. PCT/US2012/46815, filed on Jul. 13, 2012, and entitled, "MICROSCOPY WITH ADAPTIVE OPTICS," which, in turn, claims the benefit of U.S. Provisional Patent Application No. 61/507,906, filed Jul. 14, 2011, and entitled "PUPIL-SEGMENTATION BASED ADAPTIVE OPTICAL MICROSCOPY WITH FULL-PUPIL ILLUMINATION." This application also claims the benefit of U.S. Provisional Patent Application No. 61/507,906, filed Jul. 14, 2011, and entitled "PUPIL-SEGMENTATION BASED ADAPTIVE OPTICAL MICROSCOPY WITH FULL-PUPIL ILLUMINATION." Each of the above-referenced applications is incorporated herein in its entirety.

TECHNICAL FIELD

This disclosure relates to microscopy and, in particular, to microscopy with adaptive optics.

BACKGROUND

Since its invention centuries ago, light microscopy has evolved through many incarnations with distinct contrast mechanisms and hardware implementations. However, the fundamental motivation for its use has remained the same—it can resolve features that are not distinguishable by the naked eye. As a result, the push for higher resolution has been the focus of light microscopy development in recent years and several methods have been demonstrated to break the diffraction limit of conventional light microscopy. Despite all these efforts, one often underappreciated fact remains: for many biological samples, diffraction-limited resolution is rarely achieved, even for high-end research microscopes. Ideal imaging performance of a light microscope requires the excitation and/or emission light to pass through samples with optical properties identical to those of the designed immersion media, and any deviation from such conditions causes optical distortions, known as aberrations, leading to the loss of signal, image fidelity, and resolution. In practice, biological samples have inhomogeneous optical properties, so that images are increasingly degraded with increasing depth within biological tissues. For example, in point-scanning microscopes such as a two-photon fluorescence microscope, the aberrations of the excitation light result in an enlarged focal spot within the sample and a concomitant deterioration of signal and resolution.

Accordingly, there exists a need for systems and methods to address the shortfalls of present technology and to provide other new and innovative features.

SUMMARY

This disclosure describes microscopy techniques in which the directions and/or phases of individual beamlets of a light beam entering a rear pupil of an optical system are individually controlled. The individual beamlets are controlled such that the light that impinges on the rear pupil is deliberately not a plane wave but rather a wave distorted such that, after the beamlets traverse the optical system and a sample, they interfere constructively and overlap densely within the sample, thereby providing an adaptive optical correction to sample and/or system induced aberrations.

In a general aspect, a method of manipulating a focused light beam includes focusing a beam of excitation light with a lens to a focal spot within a sample, where a cross-section of the beam includes individual beamlets. Directions and/or relative phases of the individual beamlets of the excitation beam at a rear pupil of the lens are individually varied with a wavefront modulating element, and emission light emitted from the focal spot is detected while the directions or relative phases of individual beamlets are varied. The directions of individual beamlets are controlled to either maximize or minimize the emission light from the focal spot, and the relative phases of individual beamlets are controlled to increase the emission light from the focal spot.

Implementations can include one or more of the following features. For example, a location of the focal spot can be changed to a plurality of different positions within the sample, and emission light emitted from the focal spot when the focal spot is at the different positions can be detected, and an image of the sample can be generated based on the detected emission light from the different positions of the focal spot.

When the focal spot is at the different positions, directions or relative phases of the individual beamlets of the excitation beam at the rear pupil of the lens can be individually varied, with the wavefront modulating element. Emission light emitted from the focal spot can be detected while the directions or relative phases of individual beamlets are varied. The directions of individual beamlets can be controlled to either maximize or minimize the emission light from the focal spot, and the relative phases of individual beamlets can be controlled to increase the emission light from the focal spot.

The excitation light can have a first wavelength and the emission light can have a second wavelength that is less than the first wavelength. The excitation light can have a first wavelength and the emission light can have a second wavelength that is greater than the first wavelength.

The wavefront modulating element can include a reflective spatial light modulator, and a global phrase ramp can be applied to light reflected from an active layer of the spatial light modulator to induce a non-zero direction between light reflected from the active layer and light reflected from other interfaces of the spatial light modulator. The directions of individual beamlets used to maximize or minimize the emission light from the focal spot can bet determined by, for at least some of the individual beamlets varying the direction of the beamlet at the rear pupil of the lens while maintaining fixed directions of the other beamlets at the rear pupil of the lens, monitoring signal emission from the focal spot while the direction of the beamlet is varied, and based on the monitored signal emission, determining the direction of the beamlet.

For at least some of the individual beamlets, the phase of the beamlet can be varied over at least two phase values. Then, for each of the phase values, the direction of the beamlet at the rear pupil of the lens can be varied while maintaining fixed directions of the other beamlets at the rear pupil of the lens. Signal emission from the focal spot can be monitored while the direction of the beamlet is varied, and, based on the monitored signal emission, the direction of the beamlet that maximizes or minimizes the emission light from the focal spot can be determined.

For the at least some individual beamlets, the following process can be iterated at least twice: varying the direction of the beamlet at the rear pupil of the lens while maintaining fixed directions of the other beamlets at the rear pupil of the lens; monitoring signal emission from the focal spot while the direction of the beamlet is varied; and based on the monitored signal emission, determining the direction of the beamlet that maximizes or minimizes the emission light from the focal spot.

The relative phases of individual beamlets that increase the emission light from the focal spot can be determined by, for at least one of the individual beamlets: varying the phase of the beamlet at the rear pupil of the lens while maintaining fixed phases of the other beamlets at the rear pupil of the lens; monitoring signal emission from the focal spot while the phase of the beamlet is varied; and based on the monitored signal emission, determining the relative phase of the beamlet that increases the emission of signal light from the focal spot.

For the at least some individual beamlets, the following process can be iterated at least twice: varying the phase of the beamlet at the rear pupil of the lens while maintaining fixed phases of the other beamlets at the rear pupil of the lens; monitoring signal emission from the focal spot while the phase of the beamlet is varied; and based on the monitored signal emission, determining the relative phase of the beamlet that increases the emission of signal light from the focal spot.

The directions of individual beamlets that maximize or minimize the emission light from the focal spot can be determined by, for at least one of the individual beamlets: varying the direction of the beamlet at the rear pupil of the lens while maintaining fixed directions of the other beamlets at the rear pupil of the lens; dithering an optical property of the beamlet at a dither frequency; monitoring a spectral component of the signal emission from the focal spot substantially at the dither frequency while the direction of the beamlet is varied; and based on the monitored signal emission as a function of the direction of the beamlet, determining the direction of the beamlet that maximize or minimize the emission light from the focal spot.

The directions of a first beamlet and a second beamlet can be simultaneously varied at the rear pupil of the lens, and an optical property of a first beamlet can be dithered at a first dither frequency, and an optical property of a second beamlet can be dithered at a second dither frequency. Spectral components of the signal emission emitted from the focal spot substantially at the first and second dither frequencies associated with the first and second beamlets can be simultaneously monitored while the directions of the first and second beamlets are varied, and based on the monitored signal emission associated with each beamlet, the directions of the first and second beamlets that maximize or minimize the emission light from the focal spot can be determined. The first and second dither frequencies can be uncorrelated.

The cross-section of the beam can include at least N individual beamlets, with N>2, that are focused to the focal spot, the N beamlets can be provided to the rear pupil of the lens and focused to a focal spot in the sample. For the provided N beamlets, the directions of the N beamlets can be simultaneously varied at the rear pupil of the lens, and an optical property of each of the N beamlet can be dithered at a unique dither frequency. Spectral components of the signal emission emitted from the focal spot can be simultaneous monitoring substantially at the N unique dither frequencies associated with the N beamlets while the directions of the N beamlets are varied. Based on the monitored signal emission associated with each of the N beamlets, the directions of the N beamlets that maximize of minimize the emission light from the focal spot from the sample. The directions of the N beamlets can be varied by a first optical element and the optical properties of the N beamlets are dithered by a second optical element.

A reference beam can be focused to the focal spot to which the beam of excitation light is focused. For at least some of the individual beamlets, the direction of a beamlet can be varied at the rear pupil of the lens, and one or more of the individual beamlets, other than the beamlet that is varied, can be diverted away from the rear pupil of the lens. Signal emission from the focal spot can be monitored while the direction of the beamlet is varied and while the one or more individual beamlets, other than the beamlet that is varied, is/are diverted away from the rear pupil of the lens. Based on the monitored signal emission, the direction of the beamlet that maximizes or minimizes the emission light from the focal spot can be determined. Varying the direction of a beamlet at the rear pupil of the lens can include varying a position of a mirror from which the beamlet is reflected, and diverting the one or more individual beamlets, other than the beamlet that is varied, can include selecting directions with which diverted beamlets are reflected from individual micromirrors in a digital micromirror array. Varying the direction of a beamlet at the rear pupil of the lens can include varying a position of a mirror from which the beamlet is reflected, and diverting the one or more individual beamlets, other than the beamlet that is varied, can include selecting one or more phase ramps at positions on a spatial light modulator corresponding to the one or more individual beamlets to divert the one or more individual beamlets. Varying a direction of a beamlet at the rear pupil of the lens can include varying a position of a mirror from which the beamlet is reflected, and diverting the one or more individual beamlets, other than the beamlet that is varied, can include selecting directions with which diverted beamlets are reflected from individual sections of a deformable mirror.

P individual beamlets (where P is an integer), whose directions and/or relative phases are varied, can have cross-sections can overlap with each other at the rear pupil of the lens, and controlling the directions and relative phases of the P individual beamlets can include independently controlling the directions of Q different constituent beamlets at the rear pupil of the lens, where Q is an integer and Q>P.

For each of a plurality of tip angles and for each of a plurality of tilt angles of an individual beamlet, a location of the focal spot can be changed to a plurality of different positions within the sample. Then, for each of the plurality of tip angles and for each of the plurality of tilt angles and for each of the plurality of different positions of the focal spot within the sample, emission light emitted from the focal spot can be detected. Based on the emission light detected from the plurality of focal spot positions for each of the plurality of tip and tilt angles, the tip and tilt angles for a beamlet that maximize the emission light from the sample when integrated over all the positions of the focal spot can be determined.

In another general aspect, a method for increasing the intensity of light at a focal spot on an image plane of an optical system includes collecting a beam of emission light from a sample with a lens of the optical system, where a cross-section of a beam of the emission light emerging from a rear-pupil of the lens includes individual beamlets. The light beam is focused to the focal spot on the image plane, and directions and/or relative phases of the individual beamlets of the emission light beam are individually varied, with a wavefront modulating element, at the focal point. The intensity of the light at the focal spot is detected while the directions or relative phases of individual beamlets are varied, and the directions and relative phases of individual beamlets are controlled to increase the intensity of the light at the focal spot.

Implementations can include one or more of the following features. For example, the focal spot can be located at a pinhole in an opaque mask. The wavefront modulating element can include a reflective spatial light modulator and a global phrase ramp can be applied to light reflected from an active layer of the spatial light modulator to induce a non-zero direction between light reflected from the active layer and light reflected from other interfaces of the spatial light modulator.

The direction of the beamlet at the focal spot can be varied while maintaining fixed directions of the other beamlets at the focal spot, and the intensity of the light at the focal spot can be monitored while the direction of the beamlet is varied. Based on the monitored intensity, the direction of the beamlet used to increase the intensity of the light at the focal spot can be determined.

For at least some of the individual beamlets, the phase of the beamlet can be varied over at least two phase values and then, for each of the phase values: the direction of the beamlet at the focal spot can be varied while maintaining fixed directions of the other beamlets at the focal spot; the intensity of the light at the focal spot can be monitored while the direction of the beamlet is varied; and based on the monitored intensity, the direction of the beamlet used to increase the intensity of the light at the focal spot can be determined.

The relative phases of individual beamlets that increase the intensity of the light at the focal spot can be determined by, for at least one of the individual beamlets: varying the phase of the beamlet at the focal spot while maintaining fixed phases of the other beamlets at the focal spot; monitoring the intensity of the light at the focal spot while the phase of the beamlet is varied; and based on the monitored intensity, determining the relative phase of the beamlet.

The directions of individual beamlets that increase the intensity of the light at the focal spot can be determined by, for at least one of the individual beamlets: varying the direction of the beamlet at the focal spot while maintaining fixed directions of the other beamlets at the spot; dithering an optical property of the beamlet at a dither frequency; monitoring a spectral component of the intensity signal from the focal spot substantially at the dither frequency while the direction of the beamlet is varied; and based on the monitored spectral component of the intensity signal as a function of the direction of the beamlet, determining the direction of the beamlet.

The directions of individual beamlets that increase the intensity of the light at the focal spot can be determined by for at least some of the individual beamlets: simultaneously varying the directions of a first beamlet and a second beamlet at the focal spot; dithering an optical property of a first beamlet at a first dither frequency; dithering an optical property of a second beamlet at a second dither frequency; simultaneously monitoring spectral components of the intensity signal from the focal spot substantially at the first and second dither frequencies associated with the first and second beamlets while the directions of the first and second beamlets are varied; and based on the monitored spectral components of the intensity signal emission associated with each beamlet, determining the directions of the first and second beamlets.

The cross-section of the beam can include at least N individual beamlets, with N>2, that are focused to the focal spot, and the directions of individual beamlets that increase the intensity of the light at the focal spot can be determine by, for the N beamlets: simultaneously varying the directions of the N beamlets at the focal spot; dithering an optical property of each of the N beamlet at a unique dither frequency; simultaneous monitoring spectral components of the intensity signal from the focal spot substantially at the N unique dither frequencies associated with the N beamlets; and based on the monitored spectral components of the intensity signal associated with each of the N beamlets, determining the directions of the N beamlets. The directions of the N beamlets can varied by a first optical element, and the optical properties of the N beamlets can be dithered by a second optical element.

In another general aspect, a microscopy system includes a light source configured to generate beam of excitation light, where a cross-section of the beam includes individual beamlets, a lens configured to focus the beam of excitation light a focal spot within a sample, a wavefront modulating element configured to individually vary directions or relative phases of the individual beamlets of the excitation beam at a rear pupil of the lens, and a detector configured to detect emission light emitted from the focal spot while the directions or relative phases of individual beamlets are varied. The wavefront modulating element is further configured to, in response to the detected emission light, control the directions of individual beamlets to either maximize or minimize the emission light from the focal spot and to control the relative phases of individual beamlets to increase the emission light from the focal spot.

Implementations can include one or more of the following features. For example, one or more adjustable mirrors can be configured to change a location of the focal spot to a plurality of different positions within the sample, and a processor can be configured to generate an image of the sample based on the detected emission light from the different positions of the focal spot. The excitation light can have a first wavelength and the emission light has a second wavelength that is less than the first wavelength. The excitation light can have a first wavelength and the emission light has a second wavelength that is greater than the first wavelength.

The wavefront modulating element can include a reflective spatial light modulator that is configured to apply a global phrase ramp to light reflected from an active layer of the spatial light modulator to induce a non-zero angle between light reflected from a front surface of the spatial light modulator and light reflected from the active layer.

The wavefront modulating element can be further configured to vary the direction of at least some of the individual beamlet at the rear pupil of the lens while maintaining fixed directions of the other beamlets at the rear pupil of the lens, and the system can include one or more processors configured for determining the directions of the at least some individual beamlet that maximize or minimize the emission light from the focal spot based on the detected emission light that is emitted from the sample while the direction of the beamlet at the rear pupil of the lens is varied and the directions of the other beamlets at the rear pupil of the lens are maintained in fixed directions.

The wavefront modulating element can be further configured to vary the phase of an individual beamlet over at least two phase values and then, for each of the phase values to vary the direction of the beamlet at the rear pupil of the lens while maintaining fixed directions of the other beamlets at the rear pupil of the lens, and the system can further include: one or more processors configured for determining the directions of individual beamlets that maximize or minimize the emission light from the focal spot based on the detected emission light that is emitted from the sample while the direction of the beamlet at the rear pupil of the lens is varied for each of the phase values.

The wavefront modulating element can be further configured to vary the phase of an individual beamlet at the rear pupil of the lens while maintaining fixed phases of the other beamlets at the rear pupil of the lens, and the system can further include one or more processors configured to, based on the detected emission light that is emitted from the sample while the phase of the beamlet is varied, determine the relative phase of the beamlet that increases the emission of signal light from the focal spot.

The wavefront modulating element can be further configured to, for at least some of the individual beamlets, vary the direction of the beamlet at the rear pupil of the lens while maintaining fixed directions of the other beamlets at the rear pupil of the lens, and to dither an optical property of the at least some individual beamlets at a dither frequency. The detector can be further configured to detect a spectral component of the emission light substantially at the dither frequency, and the system can further include one or more processors configured to, based on the detected spectral component of the emission light as a function of the direction of the varied beamlet, determine the direction of the at least some individual beamlets that maximize or minimize the emission light from the focal spot.

The wavefront modulating element can be further configured to, for at least one of the individual beamlets, vary the direction of the beamlet at the rear pupil of the lens while maintaining fixed directions of the other beamlets at the rear pupil of the lens, and the system can further include a dithering optical element configured to dither an optical property of the at least one individual beamlet at a dither frequency, where the detector is further configured to detect a spectral component of the emission light at the dither frequency while the direction of the beamlet is varied. One or more processors can be configured to, based on the detected spectral component of the emission light as a function of the direction of the varied beamlet, determine the direction of the at least one individual beamlet that maximizes or minimizes the emission light from the focal spot.

The wavefront modulating element can include a reflective spatial light modulator and the dithering optical element can include a digital micro-mirror array or a deformable mirror. The wavefront modulating element can be further configured to, for at some of the individual beamlets, simultaneously vary the directions of the individual beamlets at the rear pupil of the lens while maintaining fixed directions of the other beamlets at the rear pupil of the lens, The dithering optical element can be configured to dither an optical property of the at least one individual beamlet at a dither frequency, and the detector can be configured to detect a spectral component of the emission light at the dither frequency while the direction of the beamlet is varied. One or more processors can be configured to, based on the detected spectral component of the emission light as a function of the direction of the varied beamlet, determine the direction of the at least one individual beamlet that maximizes or minimizes the emission light from the focal spot.

The wavefront modulating element can be further configured to, for at some of the individual beamlets, simultaneously vary the directions of the individual beamlets at the rear pupil of the lens while maintaining fixed directions of the other beamlets at the rear pupil of the lens, and a dithering optical element can be configured to dither an optical property of a first beamlet at a first dither frequency and to dither an optical property of a second beamlet at a second dither frequency. The detector can be further configured to detect spectral components of the emission light substantially at the first and second dither frequencies while the directions of the beamlets are varied. One or more processors can be configured to, based on the detected spectral components of the emission light as a function of the directions of the varied beamlets, determine the direction of first and second individual beamlet that maximizes or minimizes the emission light from the focal spot.

The cross-section of the beam can include at least N individual beamlets, with N>2, and the lens can be configured to focus the N individual beamlets to the focal spot. The wavefront modulating element can be configured to simultaneously vary the directions of the N beamlets at the rear pupil of the lens. A dithering optical element can be configured to dither an optical property of the N individual beamlets at unique dither frequencies, and the detector can be configured to detect spectral components of the emission light substantially at the N dither frequencies while the direction of the beamlets are varied. One or more processors can be configured to, based on the detected spectral components of the emission light as a function of the directions of the varied beamlets, determine the direction of N individual beamlet that maximize or minimize the emission light from the focal spot.

The wavefront modulating element can be configured to vary the direction of an individual beamlet at the rear pupil of the lens, and one or more reference beam optical elements can be configured for providing a reference beam to the focal spot to which the beam of excitation light is focused. A diverting optical element can be configured to divert one or more of the individual beamlets, other than the beamlet that is varied, away from the rear pupil of the lens. The detector can be further configured to monitor signal emission from the focal spot while the direction of the beamlet is varied and while the one or more individual beamlets, other than the beamlet that is varied, is/are diverted away from the rear pupil of the lens. One or more processors can be configured to, based on the monitored signal emission, determine the direction of the beamlet that maximizes or minimizes the emission light from the focal spot.

The diverting optical element can include a digital micromirror array configured to selectively divert individual beamlets away from the rear pupil of the lens, and varying the direction of a beamlet at the rear pupil of the lens can include varying a position of one or more mirrors of the array from which the beamlet is reflected.

The diverting optical element can be the spatial light modulator, and the spatial light modulator can be configured to apply one or more phase ramps on the spatial light modulator corresponding to one or more individual beamlets to be diverted, and the system can include one or more mirrors configured to vary the direction of the varied beamlet at the rear pupil of the lens.

The diverting optical element can include a deformable mirror that is configured to change its shape to cause one or more individual beamlets to be diverted, and one or more mirrors can be configured to vary the direction of the varied beamlet at the rear pupil of the lens.

The light source can provide P individual beamlets whose directions and/or relative phases are varied, where the P individual beamlets have cross-sections that overlap with each other at the rear pupil of the lens, where P is an integer. The wavefront modulating element can be configured to control the directions and relative phases of the P individual beamlets by independently controlling the directions of Q different constituent beamlets at the rear pupil of the lens, where Q is an integer and Q>P.

The wavefront modulating element can include a reflective spatial light modulator, a deformable mirror, or a digital micro-mirror array.

In another general aspect, a microscopy system includes a lens configured for collecting a beam of emission light from a sample, where the beam includes individual beamlets, and one or more focusing optical elements configured to focus the emission light beam to the focal spot. A wavefront modulation element is configured to individually vary directions and/or relative phases of the individual beamlets of the emission light beam at the focal spot. A detector is configured to detect an intensity of the light at the focal spot while the directions or relative phases of individual beamlets are varied, and the wavefront modulating element is further configured to, in response to the detected emission light, control the directions and relative phases of individual beamlets to increase the intensity of the light at the focal spot.

Implementations can include one or more of the following features. For example, an opaque mask defining a pinhole can be located at the focal spot.

The wavefront modulating element can includes a reflective spatial light modulator configured to apply a global phrase ramp to light reflected from an active layer of the spatial light modulator to induce a non-zero direction between light reflected from the active layer and light reflected from other interfaces of the spatial light modulator.

The wavefront modulating element can be configured to vary the direction of the beamlet at the focal spot while maintaining fixed directions of the other beamlets at the focal spot, and the detector can be configured to monitor the intensity of the light at the focal spot while the direction of the beamlet is varied, and one or more processors can be configured for determining, based on the monitored intensity, the directions of individual beamlets used to increase the intensity of the light at the focal spot.

The wavefront modulating element can be further configured to vary the phase of the beamlet over at least two phase values and then, for each of the phase values, to vary the direction of the beamlet at the focal spot while maintaining fixed directions of the other beamlets at the focal spot. The detector can be configured to monitor the intensity of the light at the focal spot while the direction of the beamlet is varied, and one or more processors can be configured for determining, based on the monitored intensity, the direction of the beamlet.

The wavefront modulating element can be configured to vary the phase of the beamlet at the focal spot while maintaining fixed phases of the other beamlets at the focal spot, and the detector can be configured to monitor the intensity of the light at the focal spot while the phase of the beamlet is varied. One or more processors can be configured to determine, based on the monitored intensity, the relative phase of the beamlet that increases the intensity of the light at the focal spot.

The wavefront modulating element can be configured to vary the direction of the beamlet at the focal spot while maintaining fixed directions of the other beamlets at the spot. A dithering optical element can be configured to dither an optical property of the beamlet at a dither frequency, and the detector can be configured to monitor a spectral component of the intensity signal at the focal spot substantially at the dither frequency while the direction of the beamlet is varied. One or more processors can be configured to determine the direction of the beamlet based on the monitored spectral component of the intensity signal as a function of the direction of the beamlet.

The cross-section of the emission beam can include at least N individual beamlets, with N>1, that are focused to the focal spot, and the wavefront modulating element can be configured to simultaneously vary the directions of the N beamlets at the focal spot. A dithering optical element can be configured to dither an optical property of each of the N beamlets at a unique dither frequency. The detector can be configured to monitor spectral components of the intensity signal from the focal spot substantially at the N unique dither frequencies associated with the N beamlets while the directions of the N beamlets are varied. One or more processors can be configured to determine, based on the monitored spectral components of the intensity signal associated with each of the N beamlets, the directions of the N beamlets that increase the intensity of the light at the focal spot.

The details of one or more implementations are set forth in the accompanying drawings and the description below. Other features will be apparent from the description and drawings, and from the claims.

BRIEF DESCRIPTION OF THE DRAWINGS

FIG. 11A is schematic diagram of a Fresnel zone plate pattern applied to a wavefront modulating element.

FIG. 11B is schematic diagram of an image of an object formed by imaging of the object with the Fresnel zone plate pattern of FIG. 11A.

FIG. 11C is schematic diagram of an array of Fresnel zone plate patterns applied to a wavefront modulating element.

FIG. 11D is schematic diagram of an array of images of an object formed by imaging of the object with the array of Fresnel zone plate patterns of FIG. 11C.

DETAILED DESCRIPTION

Figure 1:
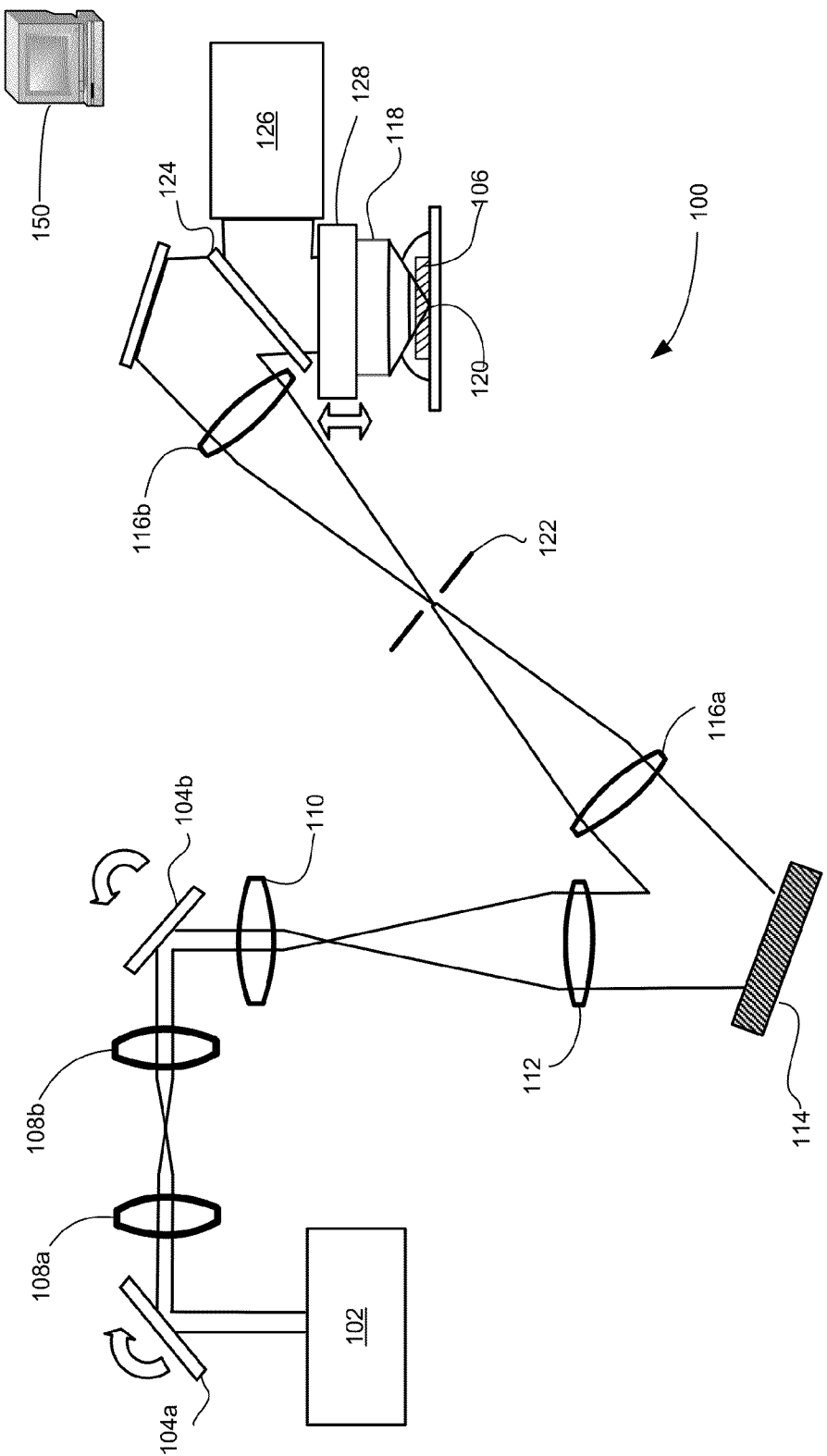
FIG. 1 is a schematic block diagram of a microscopy system that can be used for point-scanning microscopy in which adaptive optics are used to correct for system and/or sample aberrations.

FIG. 1 is a schematic block diagram of a microscopy system 100 that can be used for point-scanning microscopy of a sample in which adaptive optics are used to correct for system and/or sample aberrations. In point-scanning microscopy, light is focused into a spot having a minimal spatial extent, and signal light originating from the spot is detected with a non-imaging detector (e.g., a photo-multiplier tube). An image of an object is formed by scanning the focal spot across the sample, and computationally constructing an image from the signal light obtained from the different positions of the spot. The focal spot can be scanned within the sample by holding the sample in a fixed position and scanning the focal spot, or by maintaining a fixed position of the focal spot and moving the sample, or by a combination of moving both the sample and the focal spot.

The system includes a source 102 of excitation light. In an example embodiment, the source 102 can include a femtosecond pulsed Titanium:Sapphire laser (e.g., a model Chameleon Ultra II, available from Coherent Inc.) that produces a near-infrared beam of excitation light. The beam of excitation light can be reflected from a pair of galvanometers 104a, 104b to provide for two-dimensional (2D) raster scanning (in the x-direction and in the y-direction) of the excitation light beam and of the focal spot of the excitation beam in the sample 106. In one implementation, the galvanometers can include three millimeter beam aperture galvanometers, model number 6215H, available from Cambridge Technology Inc. The galvanometers 104a, 104b can be made optically conjugate to one another with two custom-made 30 mm focal-length telecentric f-θ lenses 108a, 108b. A third lens 110 and a custom-made 150 mm focal-length telecentric f-θ lens 112 serve to conjugate the galvanometer 104b to a wavefront modulating element ("WME") 114, and also expand the excitation beam to better match the dimensions of the WME. The sample can be mounted on a translation stage that can be used to translate the position of the sample relative to the focal spot of the excitation beam.

In one implementation, WME 114 can include liquid-crystal phase-only spatial light modulator (e.g., a 1920×1080 pixel, PLUTO-NIR spatial light modulator available from Holoeye Photonics AG). In other implementations, the WME 114 can include a deformable mirror (e.g., Mirao 52-e, available from Imagine Eyes, Inc.) or an array of micromirrors (e.g., Kilo-DM from Boston Micromachines). The WME 114 can be programmed to provide for specific AO corrections of system- or sample-induced aberrations. An advantage of using a reflective liquid-crystal phase-only spatial light modulator (SLM) as the WME is that, with a high number of pixels (e.g., 1920×1080 pixels), it can be readily divided into many subregions, each with a smoothly varying linear phase ramp therein, and in part because the subregions are truly independent, and not mechanically coupled, as in a deformable mirror. Conjugation of the galvanometers 104a and 104b to the WME 114 can allow the intensity of the excitation beam at each subregion of the WME 114 to remain constant, even during beam scanning.

The WME 114 itself can be conjugated by a pair of lenses 116a, 116b to the rear pupil plane of a microscope objective lens 118 that focuses the excitation beam to a focal spot 120 within the sample 106. In one implementation, the objective 118 can be a 20×NA 1.0 water-dipping objective with a 16 mm diameter rear pupil (e.g., model W Plan-APOCHROMAT, available from Carl Zeiss Inc.). In another implementation, the objective 118 can be a 16×NA 0.8 water-dipping objective with a 20 mm diameter rear pupil (e.g., a model LWD 16×W, available from Nikon Corp.).

Conjugation of the WME 114 to the rear pupil plane of objective 118 ensures that the corrective phase pattern applied at the WME 114 does not move across the rear pupil during scanning of the excitation beam and scanning of the focal spot 120 within the sample 106. A field stop 122 located at the intermediate image plane between the lenses 116a, 116b serves to block light from undesirable higher diffraction orders, specular reflection from the front surface of the WME (when the WME includes a reflective element, such as a SLM), and light that is reflected from subregions of the WME 114 at angles that are intended to prevent light from the subregions from entering the sample 106.

For the Zeiss objective (design NA 1.0), a $1/e^2$ beam radius σ can be 6.0 mm at the WME 114 and the rear pupil of the objective 118 for a fill-factor σ/a=0.75 normalized to the rear pupil radius a can be used. For the Nikon objective (design NA 0.8), the $1/e^2$ beam radius σ can be 6.0 mm at the WME 114, and a $1/e^2$ beam radius can be 12.0 mm at the rear pupil of the objective 118, for a normalized fill-factor σ/=1.2. These fill-factors can ensure that phase corrections can be applied over most of the excitation beam and that most of the excitation beam energy enters the objective 118. The lower fill-factor of the Zeiss objective makes the objective better suited for in vivo imaging at depth, whereas the higher fill in the Nikon case more effectively utilizes the objective NA to maximize resolution. For the Zeiss objective, the WME area used in adaptive optics correction is rectangular, while for Nikon objective, the WME area is square.

A dichroic long-pass beamsplitter 124 immediately above the objective can transmit the excitation beam light to the sample 106 and can reflect the fluorescence signal of emission light emitted from the sample 106. The reflected emission light then can be detected at a detector 126. The detector 126 can be one or more photomultiplier tubes (e.g., Model H7422-40, available from Hamamatsu). The objective 118 can be moved in the axial direction of excitation beam that impinges on the sample 106 by a z-axis stage 128. The system 100 can include one or more processors and/or computing devices 150, which may operate to control other elements of the system and or to process information obtained from the system. For example, the processors and/or computing devices 150 can operate to control the power and frequency of the light source 102, to control the position and/or angles of optical elements in the system, including mirrors and lenses, to control optical properties of the WME 114. The processors and/or computing devices 150 also can operate to process information about light detected by the detector 126. For example, the processors and/or computing devices 150 may generate an image of the sample 106 based on the detected light—e.g., when the system is used for point-scanning microscopy, the processors and/or computing devices 150 may generate an image of the sample 106 based on information about the amount and qualities of emission light when the focal spot 120 is in different positions in the sample 106.

Figure 2:
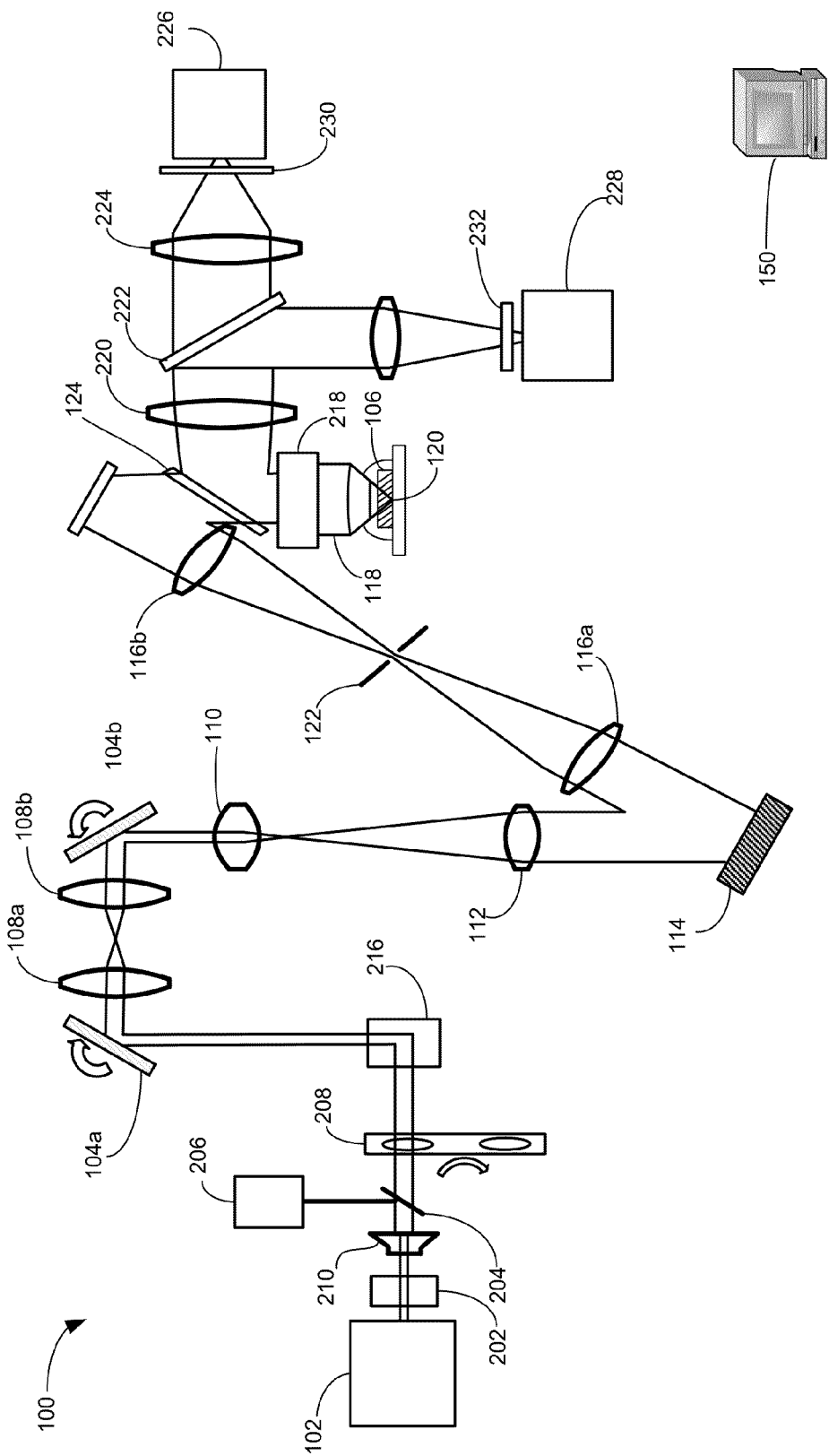
FIG. 2 is a schematic block diagram of a microscopy system that can be used for point-scanning microscopy in which adaptive optics are used to correct for system and/or sample aberrations.

FIG. 2 is a schematic block diagram of the microscopy system 100, which shows additional details of the system 100 shown in FIG. 1. Some additional details of the system include and an electro-optic modulator ("EOM") 202, (e.g., a model 350-80LA EOM, available from Conoptics Inc.) that can be combined with a beam pickoff 204 (e.g., a model 7940 beam pickoff, available from Omega Optical), a photodetector 206 (e.g., a model PDA100A photodetector, available from ThorLabs), and a proportional-integral-differential controller (not shown, e.g., a SIM960 controller, available from Stanford Research Systems) in an analog feedback loop to: 1) set the desired laser intensity at the sample; 2) stabilize the laser intensity; and c) blank the excitation beam, when the beam is not being used for scanning of the sample 106, or during fly-back of the x-galvanometer 104a while scanning. A filter wheel 208 (e.g., Lambda 10-B filter wheel, available from Sutter Instruments) with a series of neutral density filters can be used to further extend the dynamic range over which the power of the excitation beam can be reliably controlled (e.g., from 0.01% to 100% of the full power of the excitation beam). A 2× beam expander 210 (e.g, a model BE02M-B, available from Thorlabs Inc.) can be used to minimize divergence of the excitation beam over the long path from the EOM 202 to the microscope objective 118.

The microscope objective can be mounted to a fast single axis piezo flexure stage 218 (e.g., a model P-733.ZCL stage, available from Physik Instrumente, GmbH) imaging in the axial direction. Along the detection path, fluorescence can be first collimated by a lens 220 (e.g., a LA1002-A lens, available from Thorlabs), split into red and green components by a custom dichroic beamsplitter 222 (e.g., a Q560DCXR beamsplitter, available from Chroma Technology Corp.), refocused by two additional lenses 224, 226 (e.g., model LA1002-A lenses, available from Thorlabs), and then detected at the two PMTs 226, 228. Green fluorescence can be selected at the first PMT 226 with a pair of filters 230 (e.g., glass filter: model CG-BG-39-1.00-2, available from CVI, and bandpass filter: model FF01-510/84, available from Semrock), and red fluorescence can be selected at the second PMT 228 with a different filter pair 232 (e.g, bandpass filter: model FF01-617/73, available from Semrock, and bandpass filter: model FF01-630/69, available from Semrock). Low noise current amplifiers (e.g, model DLPCA-200 amplifiers, available from FEMTO Messtechnik, GmbH) can be used to boost the signals measured at the two PMTs 226, 228, and fast-resetting custom analog integrators can be used to sum the resulting amplified current spikes over the time course of each pixel, yielding two final signals that are digitized to form red and green images.

The system 100 of FIG. 1 and FIG. 2 can be used, for example, for point-scanning microscopy, including two-photon fluorescence microscopy, in thick tissues, in which a beam of excitation light having a wavelength, $\lambda$, is tightly-focused to focal spot within the sample 106, and emission light having a wavelength, $\lambda/2$, is detected from the focal spot 120 while the focal spot is scanned through the sample 106. Other microscopy techniques, including fluorescence microscopy and confocal microscopy, in which the wavelength of emission light is equal to or less than the wavelength of the excitation light, also can employ point-scanning microscopy. An image of the sample is constructed based on the emission light signal as a function of the focal spot within the sample. In point-scanning microscopy, including two-photon microscopy, aberrations that affect image quality are those experienced by the focused excitation light because they degrade the tight focus of the focal spot 120. Although the spatial intensity profile of the focal spot 120 can be calculated from electromagnetic theory, and deviations from its ideal, diffraction-limited form can be described mathematically in terms of an infinite series of aberration modes, here we instead rely on a simple physical model of focus formation that leads to an intuitive adaptive optics algorithm for aberration correction.

Figure 3:
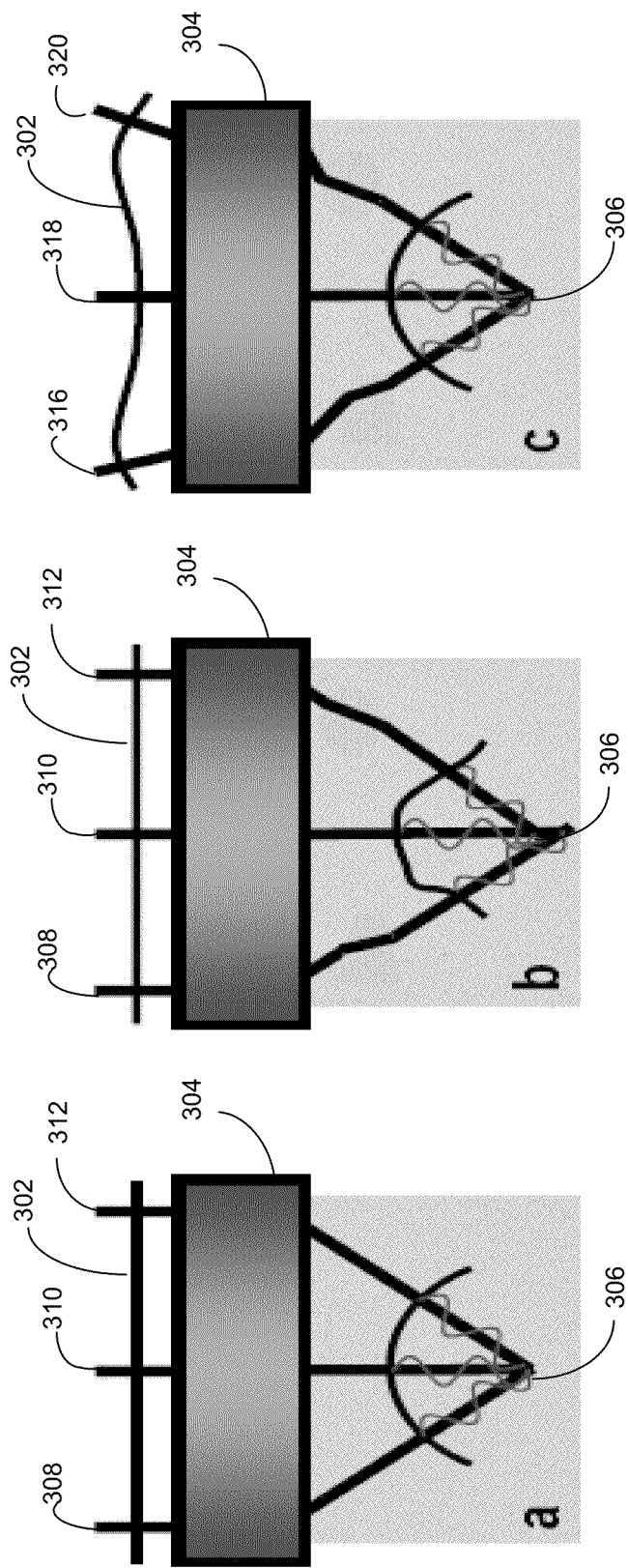
FIG. 3a is schematic diagram of a plane wave light beam impinging on an objective and being focused to a diffraction-limited focal spot without aberration.
FIG. 3b is schematic diagram of a plane wave light beam impinging on an objective and being focused to a non-diffraction-limited focal spot while suffering aberration due to inhomogeneities along the path of the wave.
FIG. 3c is schematic diagram of a distorted wave light beam composed of multiple beamlets impinging on an objective and being focused to a diffraction-limited focal spot while suffering aberration due to inhomogeneities along the path of the wave, where the aberration suffered is compensated for by the angles and the relative phases with which the beamlets enter the rear pupil of the objective.

In this model, a diffraction-limited focus 120 is viewed to arise when all light rays entering the rear pupil of the microscope objective 118 are bent to intersect at a common point with a common phase—that is, a focus is a point of maximal constructive interference. Such a condition is illustrated in FIG. 3a, where a beam that impinges on a microscope objective 304 as a plane wave 302 is focused by the microscope objective 304 to a point 306 and each example beamlet 308, 310, 312 of the beam is focused to the same focal point 306. However, as shown in FIG. 3b, unanticipated refractive index inhomogeneities along the paths between the objective 304 and the nominal focal point 306 can deflect the beamlets 308, 310, 312, so they do not all intersect at the focal point and/or can shift the relative phases of the beamlets 308, 310, 312, so that individual beamlets interfere with other beamlets at the focal point less constructively.

As shown in FIG. 3c, using an active optical element, such as the wavefront modulating element 114, optically conjugated to the rear pupil of the microscope objective, such beamlets can be individually steered back to the focal point 306, and their relative phases can be re-optimized to effectively cancel all sample induced aberrations, so that a diffraction-limited focus 306 can be obtained. When such an active optical element is used to correct for aberrations, the beam that impinges on the rear pupil of the microscope objective is not a plane wave but rather is a distorted wave 314 that includes beamlets 316, 318, 320 that impinge on the rear pupil at positions on the rear pupil, at angles to the normal of the rear pupil, and with relative phases to each other, such that they pass through the objective 304 and the sample and are tightly focused, in phase, at a focal spot having a very low spatial extent. Of course, it is not possible to individually manipulate an infinite continuum of beamlets, but it is possible to divide the active element 114 into N subregions, with each subregion having an independently adjustable phase pattern, and thereby segment the rear pupil into N beamlets individually controllable for tilt angle and relative phase offset. As the complexity of the required corrective phase pattern across the rear pupil increases, more subregions N are needed to achieve an accurate approximation. However, for a wide variety of aberrations, N<100 is usually sufficient to recover near diffraction-limited performance.

To bring the beamlets modulated by individual subregions of the WME 114 (which may include all, or a subset of all, the beamlets that illuminate the rear pupil) together at a common focal spot 120, the wavefronts (e.g., the tilt angles and relative phase offsets) of all but one beamlet can be held fixed while the wavefront of one beamlet is varied, e.g., by applying a series of phase ramps to one particular subregion of the active element 114 that corresponds to the varied beamlet. Interference between the scanned beamlet and all the other fixed beamlets modulates the intensity of the signal collected from the focal spot 120. This modulation of the collected signal can be visualized by plotting the signal relative to the angle (e.g., relative to a normal direction of the rear pupil of the objective 118). In other implementations, the modulation of the collected signal can be visualized by plotting the collected signal relative to a displacement of the beamlet in the focal plane of the objective, where the displacement of the beamlet is directly related to the angle with which the beamlet enters the rear pupil of the objective and to the focal length of the objective. In practice, the angle of the beamlet can be scanned in two dimensions to determine the optimal direction for the beamlet when it enters the rear pupil. Scanning in the two directions can be mapped to two angles relative to the normal direction of the rear pupil, where the two angles can be referred to as "tip" and "tilt" angles.

If the scanned beamlet experiences no perturbing inhomogeneities as it passes through the objective 118 in the sample 106 to focal spot 120, the 2D plot of the collected signal as a function of the tip and tilt angles of the beamlet has a maximum corresponding to zero phase ramp being applied by the portion of the active element 114 that corresponds to the scanned beamlet. However, in the presence of any perturbing inhomogeneities, the plot of the collected signal as a function of the tip/tilt angles of the scanned beamlet can have: (1) a maximum that occurs when a non-zero phase ramp is applied to the portion of the active element 114, when the scanned beamlet interferes constructively with the light from the fixed beamlets; (2) a minimum that occurs when a non-zero phase ramp is applied to the portion of the active element 114, when the scanned beamlet interferes destructively with the light from the fixed beamlets; or (3) a relatively flat intensity, if the phase of the scanned beamlet relative to the phase of the fixed beamlets is near $\pm\pi/2$. In the latter scenario, the phase of the scanned beamlet can be offset by $\pi/2$, and then the angles of the beamlet can be scanned again to yield an image with a shifted maximum or minimum, e.g., corresponding to scenario (1) or (2).

For any of the three scenarios, values of the tip/tilt angles at which the maximum or minimum in the 2D plot of the signal as a function of the tip/tilt angle of the beamlet indicates the phase ramp that needs to be applied to the subregion of the active element 114 to change the angle or direction of the beamlet corresponding to the subregion to correct for the perturbing inhomogeneities in the path of the beamlet and reduce the spatial extent of the focal spot 120. The same procedure can be applied sequentially to all of the beamlets of the excitation beam that enter the rear pupil of the objective 118 to determine the phase ramps that need to be applied to each subregion of the active element 114 to change the angle or direction (e.g., relative to a normal direction of the rear pupil of the objective 118) of all of the incoming beamlets, to compensate for perturbing inhomogeneities in the paths of each beamlet, such that the spatial extent of the focal spot 120 is reduced. The process of determining the phase ramps for each of the beamlets can be iterated multiple times, which may be useful because the initial condition of the focal spot is generally of having an aberrated focal spot, such that individual beamlets are initially interfered with a less-than-perfect focal spot formed by the combination of the remaining beamlets. Thus, after one pass through all of the beamlets to adjust the angles or directions of the beamlets, the centroid of the focal spot may be in a different position than before the process started. Therefore, iterating the process over more than one pass through the plurality of beamlets may continue to reduce the spatial extent of the focal spot 120, because, during each iteration, each beamlet is interfering with a progressively less aberrated focal spot.

After the desired angles or directions (e.g., relative to a normal direction of the rear pupil of the objective 118) of the individual beamlets (or, equivalently, the phase ramps on subregions of the active element 114 corresponding to the individual beamlets) have been determined, the relative phases of the individual beamlets can be varied to determine the relative phases of the individual beamlets that result in maximal constructive interference at the focal spot 120. In another implementation, to correct the phase of the individual beamlets, information about the beam deflection angles applied by the active element 114 to bring the individual beamlets together to intersect in a common focal spot can be used to define an array of phase gradient measurements across the rear pupil of the objective. From these phase gradient measurements, the relative phases of the individual beamlets at the rear pupil necessary for the individual beamlets to interfere constructively at the focal spot 120 can be determined through an interative algorithm based on the known spatial continuity of the phase across the wavefront, as described in Panagopoulou, S. I., Neal, D. R., "Zonal matrix iterative method for wavefront reconstruction from gradient measurements," *J. Refract. Surg.* 21, S563-S569 (2005) or Ji, N., D. E. Milkie, and E. Betzig, "Adaptive optics pupil segmentation for high-resolution imaging in biological tissues." *Nature Methods,* 2010. 7(2): p. 141-147, both of which are incorporated herein by reference.

These adaptive optics techniques can be particularly useful when the objective 118 includes a gradient-index (GRIN) lens. GRIN lenses can be desirable because they can be inserted into biological tissue to image deeper regions normally inaccessible to optical imaging using conventional objective lenses external to the sample. However, GRIN lenses suffer from relatively high aberrations compared to conventional lenses. The adaptive optics techniques described herein can compensate for the aberrations in the GRIN lenses.

In some implementations the active element 114 can include a spatial light modulator that scans the angles of the beamlets by applying varying phase ramps to subregions of the active element that correspond to the individual beamlets. In other implementations, the active element 114 can be a deformable mirror (e.g., a piston-tip-tilt mirror) or a micromirror array that can scan the angles of the beamlets by changing orientations of the region of the mirror or mirror array that correspond to individual beamlets.

In the "on" subregions, when the WME includes a reflective element, such as a SLM, a gentler, global phase ramp can be applied to separate the large fraction of light modulated within the WME 114 from the small fraction of light specularly reflected from the front surface of the WME, which cannot be controlled. The global ramp can also separate the modulated light from the unmodulated light due to the less-than-perfect diffraction efficiency. After adaptive optics correction, another, local phase ramp, that is unique to each subregion of the WME 114 can be is superimposed upon the global phase ramp to produce the necessary correction to the tilt angle and phase of the individual beamlets required to create a diffraction-limited focal spot 120 in the sample 106. In one implementation, individual pixels of the WME can be programmed with one of 256 different grayscale values. The relationship between the 8 bit grayscale level used to control the WME and the actual phase shift produced in a beamlet modulated by a pixel is determined by calibration according to the manufacturer's recommendations.

For both the tip/tilt angle and phase measurement portions of the adaptive optics process, a background image with all subregions "off" can be acquired whenever the power level is changed, and the background image can be subtracted from all subsequent images acquired at the same power level, to insure the accuracy of the measurements.

In some implementations, an optical property of a beamlet can be dithered (i.e., rapidly changed in a periodic manner) at a dither frequency while an angle of the beamlet is being varied and angles of other beamlets are held fixed. Then, the collected signal can be monitored by though a frequency-based technique. For example, in some implementations, a lock-in amplifier tuned to the dither frequency can be used to monitor the signal emitted from the focal spot as a function of the dither frequency. In other implementations, a fast Fourier transform ("FFT") can be applied to the detected signal to extract the frequency-dependent information from the signal. For example, the intensity, phase, tip/tilt angle, or polarization of the scanned beamlet can be dithered at the dither frequency while the angle of the scanned beamlet is scanned across a variety of angles. For example, when the active element 114 is a spatial light modulator the intensity of the beamlet can be dithered by modulating the diffraction efficiency of the subregion of the spatial light modulator corresponding to the beamlet, while simultaneously varying and angle of the beamlet by applying different phase ramps to the subregion of the spatial light modulator. Similarly, the phase of the beamlet can be dithered by the subregion of the spatial light modulator corresponding to the beamlet, while simultaneously varying an angle of the beamlet. By using frequency-based detection, a spectral component of the detected signal substantially at the dither frequency (i.e., having a center frequency and bandwidth sufficient to discriminate the dithered signal from noise or other signals at other dither frequencies) can be recorded, and the modulation of the collected signal due to the interference between the scanned beamlet and the other fixed beamlets can be extracted with a relatively high signal to noise ratio.

In some implementations, an optical property of the first beamlet can be dithered at a first dither frequency, and an optical property of a second beamlet can be dithered at a second dither frequency, while simultaneously varying the angles of both the first and second beamlets. Then, the collected signal can be monitored simultaneously at the first and second dither frequencies using frequency-based techniques to extract information about the interference of the first and second beamlets with the other beamlets of the excitation beam. In this manner, angles or directions of the first and second beamlets that should be used to reduce the spatial extent of the focal spot can be determined in parallel, rather than in a sequential manner.

In some implementations, the variation in the angles of the first and second beamlets generally can be uncorrelated, to avoid sweeping the first and second beamlets together across the rear pupil of the objective in a manner that significantly changes the position or size of the focal spot. In addition, the first and second frequencies can be uncorrelated so that the frequency-based detection system does not detect an appreciable signal at the first dither frequency due to modulation of the second beamlet, and such that a lock-in amplifier tuned to the frequency-based detection system does not detect an appreciable signal at the second dither frequency due to modulation of the first beamlet. For example, within detection limits of the detector, the first dither frequency and the second dither frequency are not harmonics of each other and/or are a ratio of the first dither frequency to the second dither frequency is not a rational number.

In some implementations, the optical properties of each of N>2 beamlets can be dithered at its own unique frequency while the directions or angles of the N beamlets at the rear pupil of the objective are varied. The signal emitted from the focal spot can be simultaneously monitored at the N unique dither frequencies while the angles or directions of the N beamlets are varied. Then, based on the monitored signals, the angles or directions of the N beamlets that should be used to reduce the spatial extent of the focal spot can be determined in parallel.

In some implementations, rather than determining the optimal tip and tilt angles for individual beamlets based on emission of light from a single focal point, the optimal angles can be determined based on integrated information from a plurality of focal points within the sample. For example, the focal point can be scanned to a plurality of positions within the sample for each of a plurality of different tip and tilt angles. Emission light can be detected from each of the focal points for each of the tip and tilt angles. The optimal tip and tilt angles for a particular beamlet can be determined based on the detected emission light received from each of the plurality of focal points. For example, in some implementations, the optimal tilt angles for a particular beamlet can be determined as the tip and tilt angles that maximize the emission of light integrated over all of the focal points. Particular implementations described herein for determining optimal tip and tilt angles for individual beamlets based on the detection of the mission light from a single focal point (e.g., dithering of an optical property of a beamlet, etc.), also can be used when determining the optimal tip and tilt angles based on detection of emission light integrated over a plurality of focal points.

Figure 4:
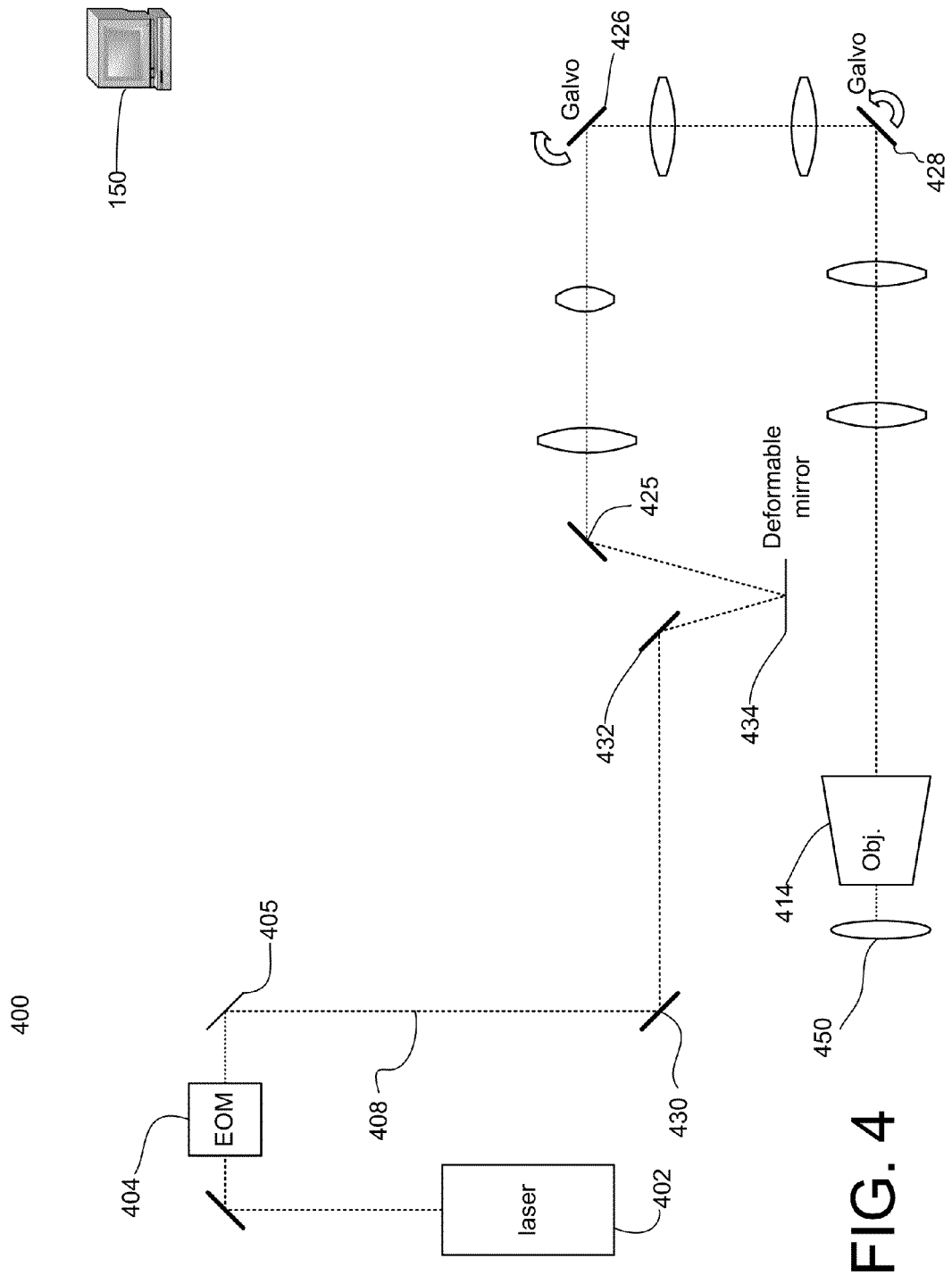
FIG. 4 is a schematic block diagram of a microscopy system that can be used for point-scanning microscopy in which adaptive optics techniques are used to reduce the spatial extent of the focal spot of the excitation beam.

FIG. 4 is a schematic block diagram of a microscopy system 400 that can be used for point-scanning microscopy in which adaptive optics techniques are used to reduce the spatial extent of the focal spot of the excitation beam. The system 400 includes a light source (e.g., a laser) 402. An electro-optic modulator 404 can be used to control the intensity of the beam delivered to the system. A mirror 405 directs an excitation beam 408 toward a mirror 430 and then to a mirror 432 that directs the beam 408 toward a deformable mirror 434 that also can act as an active element in the system 400 to vary the tip and tilt angles and/or the phase of individual beamlets that impinge on a rear pupil of the objective 414. The beam that results from modulation by deformable mirror 434 is reflected off a mirror 425 and a pair of galvo mirrors 426, 428, through the objective lens 414 and focused within a sample 450.

The deformable mirror 434 can include a micromirror array in which individual micro-mirrors of the array are capable of tip, tilt and piston motion. The deformable mirror can be used to perform adaptive optics techniques in which angles of individual beamlets are varied serially or in parallel. In some implementations, dithering of individual beamlets can be introduced either by intensity modulation (e.g., by changing the tip and/or tilt angles of individual beamlets to direct them away from entering the back pupil of the objective 414) or by phase modulation (e.g., by changing the length of a beam path 408 for an individual beamlet through piston motion control of the micro-mirrors). A plurality of beamlets can be dithered simultaneously through control of individual subregions of the mirror 434 for parallel measurements, as described above.

Figure 5:
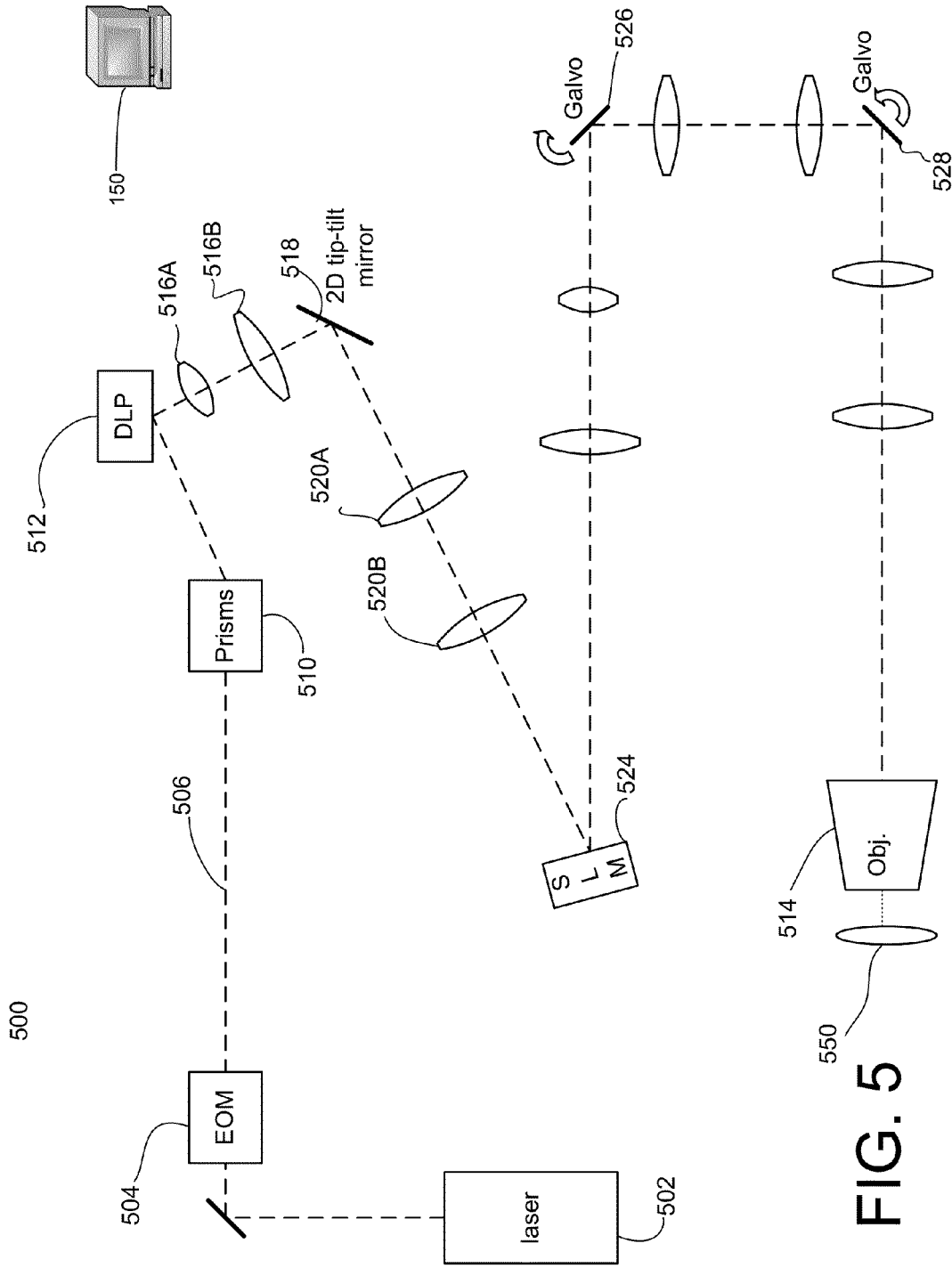
FIG. 5 is a schematic block diagram of another microscopy system that can be used for point-scanning microscopy in which adaptive optics techniques are used to reduce the spatial extent of the focal spot of the excitation beam.

FIG. 5 is a schematic block diagram of another microscopy system 500 that can be used for point-scanning microscopy in which adaptive optics techniques are used to reduce the spatial extent of the focal spot of the excitation beam. The system 500 includes a light source (e.g., a laser) 502. An electro-optic modulator 504 can be used to control the intensity of the beam delivered to the system. One or more prisms 510 refract light toward a digital micro-mirror device 512. The micro-mirror device 512 is optically conjugated by a pair of lenses 516A, 516B to a fast two-dimensional galvo mirror 518 that can be used to vary the tip and tilt angles of the beam 506. In another implementation, two galvo mirrors that direct the light on orthogonal axes can be used in place of the mirror 518. The galvo mirror 518 can be optically conjugated by a pair of lenses 520A, 520B to a spatial light modulator 524. The spatial light modulator 524 also can act as an active element in the system 500 to vary the tip and tilt angles and/or the phase of individual beamlets that impinge on a rear pupil of the objective 514. After interacting with the spatial light modulator 524, the beam of excitation light is reflected off of two galvo mirrors 526, 528 optically conjugated to the rear pupil of the objective 514, which can be used to scan the focal spot of the excitation beam to a plurality of different positions within a sample 550.

The digital micro-mirror device 512 can be used in conjunction with the spatial light modulator 524 to vary the tip and tilt angles of a beamlet at a relatively low rate while dithering an optical property of the beamlet at a relatively fast rate. The digital micro-mirror device 512 can be used to modulate the intensity of individual beamlets that reach the sample 550 by using one or more individual mirrors to quickly change the path of a beamlet.

Because the response time of the digital micro-mirror device 512 is faster than the response time of the spatial light modulator 524, the digital light modulator can be used to apply a dither frequency in the 1-100 kilohertz range, while the spatial light modulator is used to vary the tip and tilt angles at a rate in the tens to hundreds of hertz range. In some implementations, a deformable mirror can be used in place of the digital micro-mirror device 512 to provide the fast dither frequency by angle, phase, or intensity modulations, because the response time of a deformable mirror is also relatively fast compared with the response time of a spatial light modulator.

The prisms 510 are used in conjunction with the digital micro-mirror device 512, because, due to the way the micro-mirrors in the digital micro-mirror array 512 are arranged, for coherent light source 502, the device 512 acts as a blazed grating. Because light source 502 may not be monochromatic, the different frequency components diffracted off the digital micro-mirror array 512 would have both temporal and spatial dispersions, which, if not compensated, would cause the frequencies to spatially spread out and temporally separated at the focus. The prisms 510 therefore introduce temporal and spatial dispersions of opposite signs to those caused by the device 512. Frequency filters other than prisms also can be used to provide such functionality. Other active elements, e.g., a deformable mirror or a digital micro-mirror array, also can be used in place of the SLM 524 to vary the tip and tilt angles of individual beamlets of the excitation beam to determine the optimal angles or directions of the beamlets that should be used to provide a focal spot with a reduced spatial extent. Other active elements also can be used in place of the digital micro-mirror array 512 to modulate an optical property of the individual beamlets of the excitation beam. For example, a deformable mirror could be used to vary the phase of the beamlets.

The combination of using a fast active element, e.g., a digital micro-mirror device or a deformable mirror (e.g., a fast tip-tilt-piston segmented mirror) and a spatial light modulator 524 also can be used when acquiring a three-dimensional images of a sample as the focal spot is scanned axially (i.e., along an axis of the excitation beam) through a sample. For example, when the fast active element is used to vary the angles of the beamlets to determine the optimal angles for the beamlets, as aberrations increase when imaging more deeply into the sample, the corrections found quickly by the fast active element as a given depth in the sample can be applied to the spatial light modulator, so that the fast active element only needs to correct for the additional aberrations when proceeding to the next depth in the sample.

The combination of using a fast active element, e.g., a digital micro-mirror device or a deformable mirror (e.g., a fast tip-tilt-piston segmented mirror) and a spatial light modulator 524 also can be used to take advantage of the relatively fast speed of the fast active element and to take advantage of the relatively higher pixel density of the spatial light modulator. For example, the fast active element can be used to vary the angles of the beamlets to determine the optimal angles for the beamlets when the fast active element is in a first position. Then, the information about the determined optimal angles can be transferred to the spatial light modulator, and the fast active element can be translated laterally by a fraction of the spacing between adjacent segments of the digital micro-mirror device or by a fraction of the spacing between adjacent elements of the deformable mirror. When the fast active element is in the new position, it can again be used to vary the angles of the beamlets to determine the optimal angles for the beamlets, and the information about the determined optimal angles when the fast active element is in the new position can be transferred to the spatial light modulator. The arrays of beamlets for which the optimal angles are determined when the fast active element is in the first position and in the new position are laterally offset from each other at the rear pupil of the objective 514. The process of laterally translating the fast active element and determining optimal angles for a new array of beamlets can be repeated multiple times to achieve an increasingly dense set of measurements for the optimal angles of beamlets across the rear pupil of the objective 514. Finally, these measurements can be combined by phase reconstruction to recover the final, densely sampled, corrective wavefront that should be applied to the spatial light modulator 524 to reduce the spatial extent of the focal spot within the sample.

The different active elements (e.g., the digital micro-mirror device 512 and the spatial light modulator 524) can be used individually or in combination with each other to perform the adaptive optics techniques described above. For example, each of the active elements 512, 524 can be used individually to perform the adaptive optics techniques described above in relation to FIGS. 1-3. In addition, combinations of two or more active elements 512, 524 can be used to perform adaptive optics techniques to reduce the spatial extent of a focal spot formed by the objective 514 in a sample.

Figure 6:
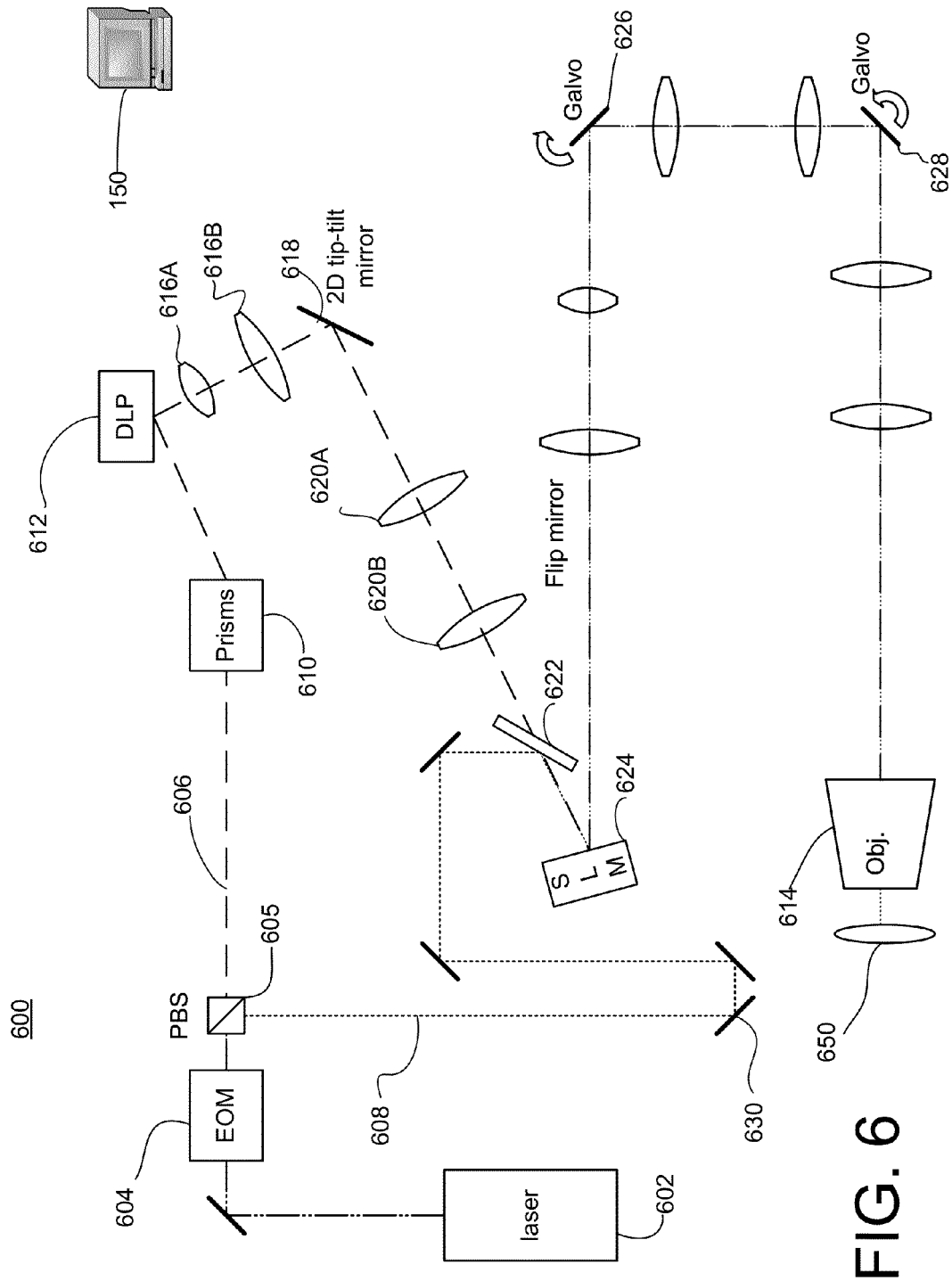
FIG. 6 is a schematic block diagram of another microscopy system that can be used for point-scanning microscopy in which adaptive optics techniques are used to reduce the spatial extent of the focal spot of the excitation beam.

FIG. 6 is a schematic block diagram of another microscopy system 600 in which a reference beam that illuminates the entire rear pupil of the objective 614, or a large portion of the rear pupil, is mixed with one or more individual beamlets of the excitation beam, and interference between the reference beam and the individual beamlets can be observed to determine the optimal angles for the one or more individual beamlets that would achieve a reduction in the spatial extent of the focal spot.

The system 600 includes a light source (e.g., a laser) 602. An electro-optic modulator 604 can be used to control the intensity of the beam delivered to the system. A polarizing beam splitter 605 splits the beam of excitation light and directs a beam 606 toward one or more prisms 610 that refract light toward a digital micro-mirror device 612. The micro-mirror device 612 is optically conjugated by a pair of lenses 616A, 616B to a fast two-dimensional galvo mirror 618 that can be used to vary the tip and tilt angles of the beam 606. In another implementation, two galvo mirrors that direct the light on orthogonal axes can be used in place of the mirror 618. The galvo mirror 618 can be optically conjugated by a pair of lenses 620A, 620B, through a beam combiner 622 to a spatial light modulator 624. The spatial light modulator 624 can act as an active element in the system 600 to vary the tip and tilt angles and/or the phase of individual beamlets that impinge on a rear pupil of the objective 614. After interacting with the spatial light modulator 624, the beam of excitation light is reflected off of two galvo mirrors 626, 628 optically conjugated to the rear pupil of the objective 614, which can be used to scan the focal spot of the excitation beam to a plurality of different positions within a sample 650.

The beam splitter 605 also creates a second beam 608 that serves as the reference beam. The reference beam passes through a delay line 630 and then reflects off the beam combiner 622 to mix with beam 606, and then reflects off of spatial light modulator 624, reflects off the galvo mirrors 626, 628, then passes through the objective 614 and into the sample 650

In this configuration, individual beamlets of the excitation beam 606 can be dithered by particular corresponding regions of the digital micro-mirror array 612, while other beamlets are turned off by corresponding regions of the digital micro-mirror array 612 or by corresponding regions of the spatial light modulator, such that the "off" beamlets do not impinge on the rear pupil of the objective 614.

The angles with which the individual "on" beamlet enters the rear pupil of the objective can be varied rapidly by a fast galvo mirror 618 that can sweep the "on" beamlet in two dimensions, and interference between the reference beam and the "on" beamlet(s) in the light emitted from the sample can be used to determine the optimal angle for the "on" beamlet. The galvo mirrors 626, 628 can be used to maintain a fixed position of the "on" beamlet on the rear pupil of the objective, while the angle with which the "on" beamlet enters the rear pupil is varied by the tip-tilt mirror 618. This process can be repeated for all of the beamlets of the excitation beam that enter the rear pupil of the objective, and information about the optimal angles for the individual beamlets then can be mapped onto the spatial light modulator 624 to provide a focal spot within the sample having a reduced spatial extent. Because the galvo mirror 618 can be used to vary the angle of the individual beamlets faster than the spatial light modulator 624 could, use of the two-dimensional tip-tilt mirror 618 to discover the optimal angles of individual beamlets in a serial manner can be faster than using the spatial light modulator 624 in such a manner.

The reduction in the aberration of excitation beam light at the focal spot of the sample and the improvement in the resulting images obtained from the sample generally increases monotonically as a function of the number of subregions, N, of an active element, which correspond to individual segments of the rear pupil of the objective, although at some value of N the improvement in resolution and signal strength reaches saturation. The number of subregions N required to achieve good results will depend on the specifics of the sample under investigation, the parameter being optimized, and the degree of optimization desired. The density of subregions on an active element, which corresponds to individual segments of the rear pupil of the objective, does not have to be uniform across the active element. Rather, an initial low resolution map of the aberrated wavefront can be made using a low N value, and then the areas suggestive of fine structure can be sampled with a higher density of subregions.

Aberrations affecting the performance of the microscope system can come from anywhere along the optical path between the light source and the focal spot, as well as from the sample itself. Thus, these intrinsic microscope aberrations can be characterized in order to be able to derive the sample-induced component of the total measured aberration in subsequent experiments. For example, an image may be acquired of a fluorescent bead reference object, and the image may show significant astigmatism and coma that may be largely attributable to poor flatness of an active element. However, after applying the adaptive optics correction described herein with N=36 independent subregions and direct phase measurement, the full width at half maxima (FWHM) of the bead images in both the lateral (X-Y plane) and axial (X-Z, Y-Z, long axis-Z, and short axis-Z planes) directions can approach their diffraction-limited values.

After the adaptive optics process is completed and the phases to be applied to the active element subregions, which result in individual beamlets having the proper angles and phases at the rear pupil of the objective to achieve a diffraction-limited focal spot, have been determined, the phase pattern on the an active element represents the final corrective wavefront, modulo $2\pi$. To display this wavefront in a more intuitive form, the global phase ramp used during measurement is subtracted, and the phase is unwrapped by counting fringes and assuming that the phase is continuous across subregion boundaries. Finally, to determine the aberration due to the sample alone, the portion of the unwrapped wavefront due to system aberrations is subtracted.

Figure 7:
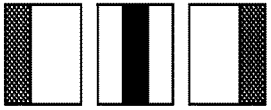
FIG. 7a is a schematic diagram of a three independent masks on a wavefront modulating element that are used to segment a beam on a rear pupil of an objective.
FIG. 7b is a schematic diagram of a nine independent masks on a wavefront modulating element that are used to segment a beam on a rear pupil of an objective.
FIG. 7c is a schematic diagram of a six masks on a wavefront modulating element that overlap to create nine segments at a rear pupil of an objective.
FIG. 7d is a schematic diagram of a fifteen masks on a wavefront modulating that are positioned in multiple positions to overlap with each other to create 18 segments at a rear pupil of an objective.

In addition to applying the adaptive optics correction described herein with independent subregions of a wavefront modulating elements, FIGS. 7a, 7b, 7c, and 7d, provide examples of how the independent, overlapping, and stepped overlapping mask approaches to adaptive optics correction. The rear pupil of the objective 118 is represented by the large squares in each of the figures, and the shaded rectangles represent the fraction of the pupil turned on at specific points during beam deflection measurements. In the independent mask approach, shown in FIGS. 7a and 7b, the rear pupil of the objective 118 is segmented into non-overlapping areas by utilizing different corresponding subregions of the wavefront modulating element to perform adaptive optics on the beam. Each area, or "mask," is turned "on" individually during the beam deflection measurements. The corrective wavefront in each masked subregion of the wavefront modulating element is estimated by a plane independent from that in all other regions. FIG. 7a illustrates the independent mask approach, in which three non-overlapping masks for the WME 114, each corresponding to ⅓ of the total pupil area, independently measure beam deflection and correct for aberration in each of three pupil subregions. FIG. 7b illustrates the independent mask approach, in which nine non-overlapping masks for the WME 114, each corresponding to ⅑ of the pupil area, independently measure beam deflection and correct for aberrations in each of nine pupil subregions.

In the overlapping mask approach, shown in FIG. 7c, masks that are individually "on" during beam deflection measurement overlap with other masks. As a result, the total number of planar subregions in the final corrective wavefront is larger than the ratio of the pupil area to the mask area. However, the final values of phase in these subregions may not be fully independent from one another, due to mask overlap. On the other hand, for a given mask area, or equivalently, a given laser power, overlapping masks allows many more subregions to be used, and thus often leads to superior correction. Thus, FIG. 7c illustrates the overlapping mask approach, in which six overlapping masks for the WME 114, each covering ⅓ of the pupil area, lead to unique wavefront estimations for each of nine different pupil subregions. Therefore, in general, wherein P overlapping individual beamlets can have their directions and/or relative phases varied, where P is an integer. Then, based on the signal light detected as the P overlapping beamlets are varied, Q beamlets at the rear pupil of the objective can be independently controlled to maximize the intensity of the emission light from the focal spot, where Q is an integer, and Q is greater than P.

Finally, in the stepped overlapping mask approach, shown in FIG. 7d, masks have the same dimensions, but are displaced from their neighbors by a distance less than the dimension of the mask. For example, the pattern described in FIG.

7d is denoted 3×3 with 2×1 stepped overlapping masks, where "3×3" denotes the dimension of each mask (three horizontal×three vertical masks to span the rear pupil), and "2×1" denotes the stepping pattern (two steps to cross the width of each mask, and one step to cover the height). This approach is particularly well suited to phase reconstruction, since it permits a dense array of phase gradient data to be measured on a regular interval. Thus, in the stepped overlapping approach, an aberrated wavefront can be measured on a scale smaller than the size of a single "on" subregion by using subregions in a series of discrete steps smaller than subregion itself and measuring the beam deflection within the focal plane of the objective, and thus the phase gradient, at each step. FIG. 7d illustrates the stepped overlapping mask approach, in which a mask for the WME 114 covering ⅑ of the pupil area is translated in horizontal steps equal to half the width of the mask, and in vertical steps equals to the height of the mask. Beam deflection is measured at each position of the mask. Thus, FIG. 7d is denoted as 3×3 with 2×1 stepped overlapping masks, such that the mask corresponding to ⅑ of the pupil area, leads to unique wavefront estimations for each of 18 different pupil subregions. Phase reconstruction can be used to determine the optimal phase offset at each position of the stepped overlapping mask, and combined with the gradient data to determine the plane of best fit to the aberrated wavefront in the region centered at each measurement point.

The overlapping and stepped overlapping mask approaches can be extended further, such that, for example, N=81 subregions of the rear pupil can be defined using masks that correspond to ⅑ the area of the rear pupil. Of course, for a given number of subregions, N, the independent mask approach outperforms the overlapping or stepped overlapping mask approaches, due to residual coupling between the subregions. However, for a given mask area, or equivalently, a given laser power, overlapping or stepped overlapping masks allows many more subregions to be used, and thus often leads to superior correction.

In addition to being used for point-scanning microscopy, as described above, adaptive optics also can be used to enhance the quality of images obtained through widefield microscopy. In widefield microscopy, a large region of the sample is uniformly illuminated and the entire region of interest is recorded simultaneously on an imaging detector (e.g., a CCD camera). For most point-scanning methods, the major effect of aberration is on the excitation light, preventing the formation of a diffraction-limited focus. The major effect of aberration, as described above, is then on the emission path, preventing the signal emitted from each point in the sample from being refocused to a diffraction-limited spot at the imaging detector. Point-scanning microscopy may be preferred in scattering biological tissues, and widefield-scanning microscopy may be more commonly applied to transparent biological samples, but sample-induced aberration is common in either case.

Figure 8:
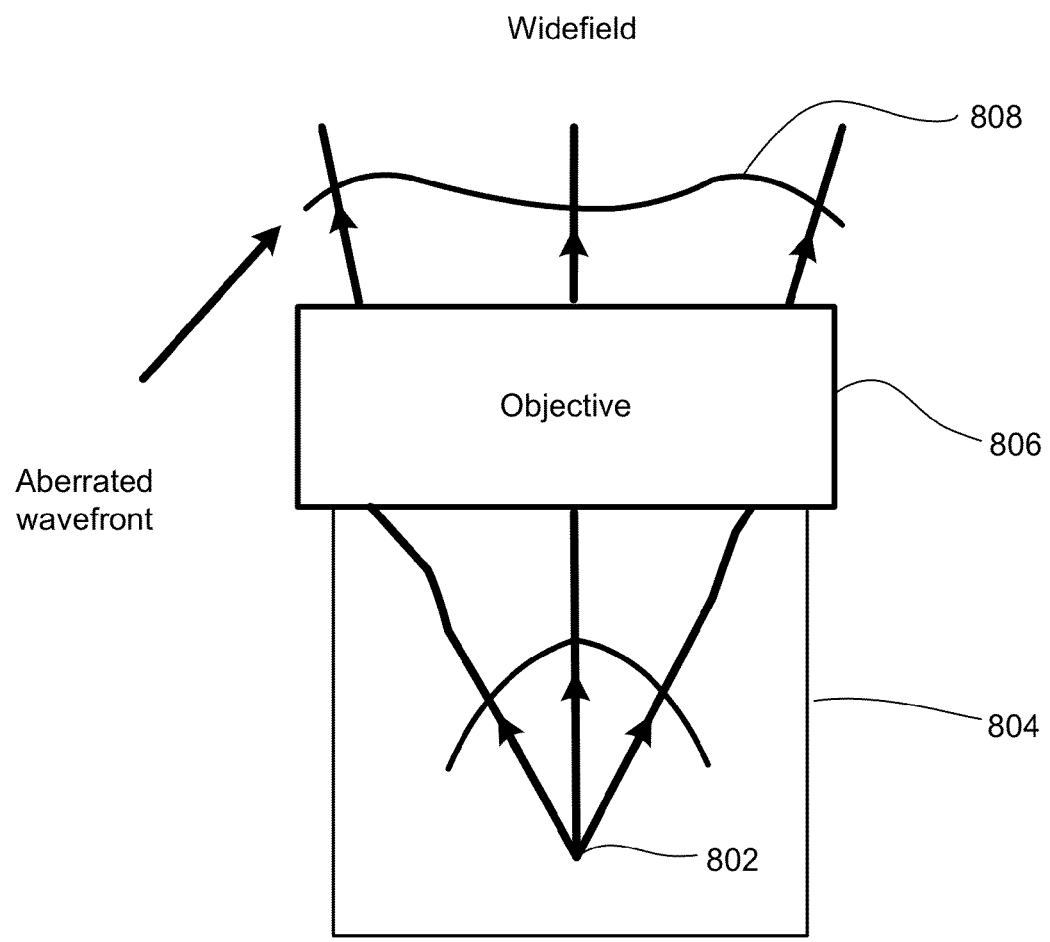
FIG. 8 is a schematic diagram of a sample that induces aberrations to light that passes through the sample.

For example, as shown in FIG. 8, a spherical wave front of emission light can be emitted from a point 802 in a sample 804. The wave front can be distorted (i.e., aberrated) by index of refraction inhomogeneities in the sample 804. Then, collimating the aberrated wavefront by a microscope objective 806 does not result in a plane wave, but in an aberrated wave front 808.

Unlike point scanning microscopy, conventional widefield microscopy generally lacks strong optical sectioning ability. Thus, it is usually used for single cultured cells and ultrathin tissue sections, where aberration is typically not an issue. However, with the recent development of widefield methods having axial sectioning capability, such as selective plane illumination microscopy ("SPIM") and structured illumination microscopy ("SIM"), application to thick samples is now possible, so correcting the aberration of the emitted light becomes relevant.

Figure 9:
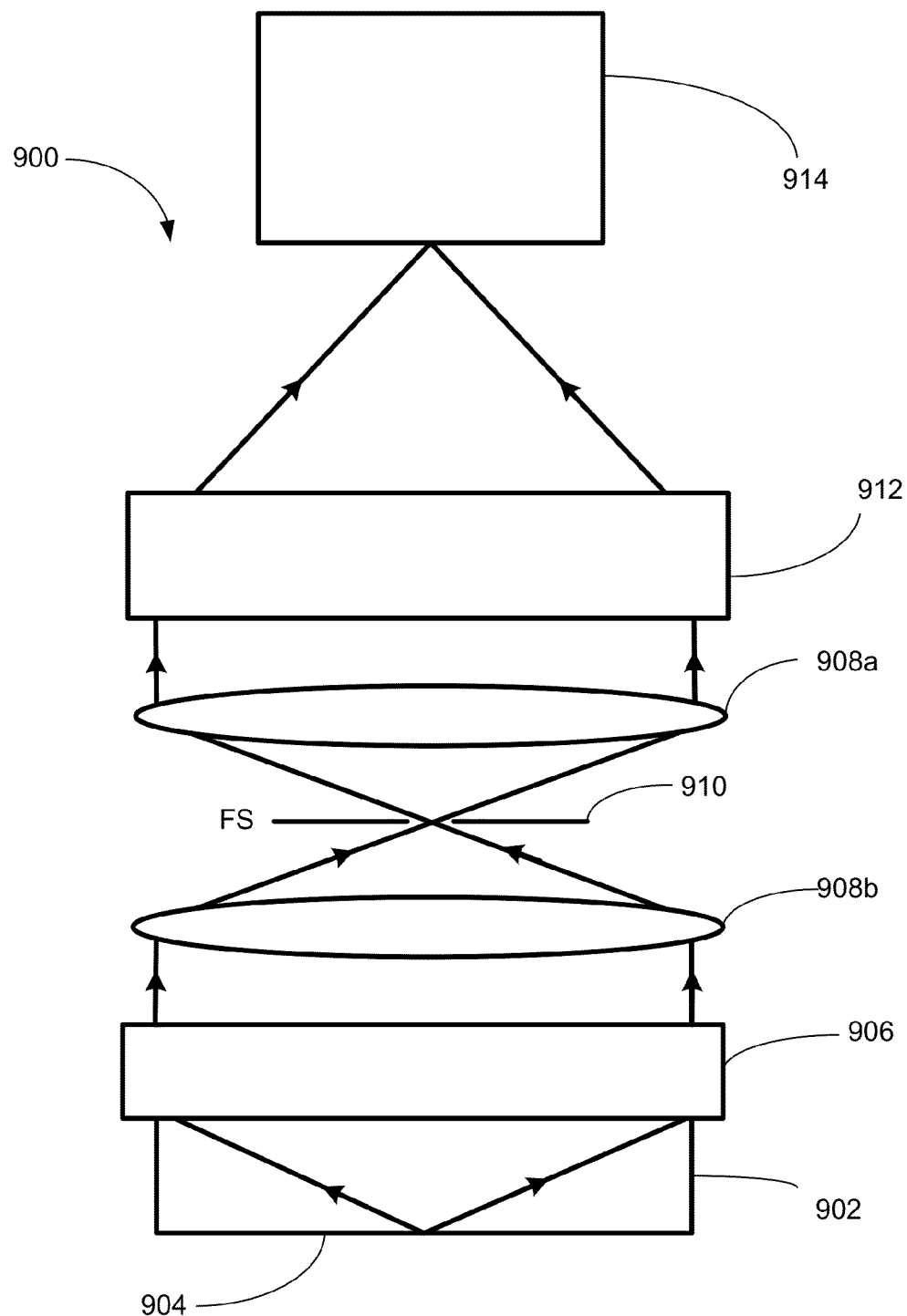
FIG. 9 is a schematic diagram of a widefield microscopy system that corrects aberrations using adaptive optics techniques.

FIG. 9 is a schematic diagram of a widefield microscopy system 900 that corrects aberrations using adaptive optics techniques. Emission light emitted from a focal plane 904 of the system 900, where the focal plane lies within a sample 902. An objective lens 906 collimates the emitted light, which may suffer aberration due to passage through the sample 902, and a pair of telescoping lenses 908a, 908b can be used to pass the focused light through a field stop 910 and to expand or reduce the waist of the beam of emission light. A wavefront modulating element 912 then applies adaptive optics techniques to the aberrated wave front before passing the emission light to a detector 914. The WME 912 can apply similar adaptive optics techniques described above with respect to point-scanning microscopy, to apply individual shifts in angles of beamlets of the emission light beam from the focal plane 904, such that images formed with different parts of the wavefront can be used to reconstruct a complete diffraction-limited widefield wavefront. In the widefield microscopy 900 it is the emission light beam to which the adaptive optics techniques are applied, as opposed to applying adaptive optics techniques to the excitation light beam in the point-scanning microscopy systems described above.

Figure 10:
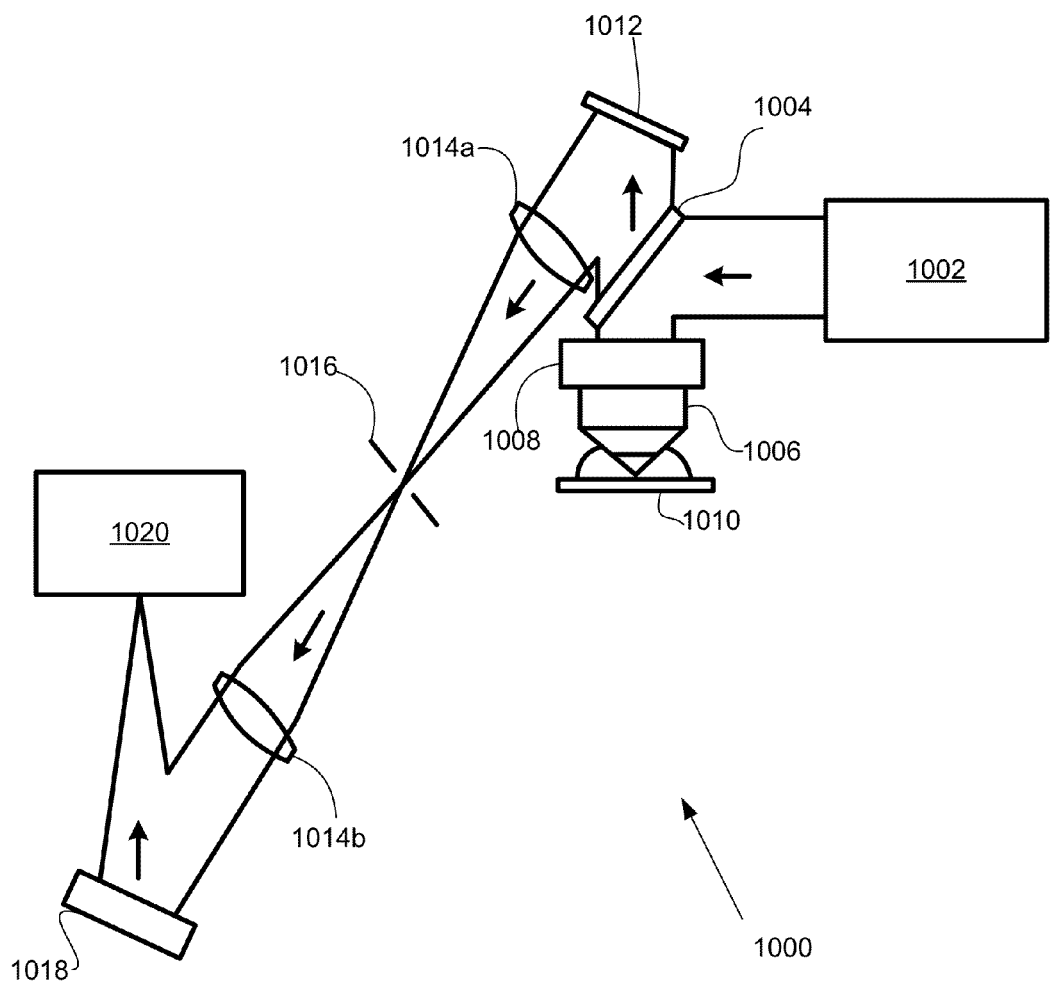
FIG. 10 is a schematic diagram of a widefield microscopy system that corrects aberrations using adaptive optics techniques.

FIG. 10 is a schematic diagram of a widefield microscopy system 1000 that corrects aberrations using adaptive optics techniques and shows additional details of the system 1000. A source of excitation light 1002 provides excitation light that is reflected from a beam splitter 1004 through an objective lens 1006 mounted on a translation stage 1008 into a sample 1010. Emission light is emitted from the sample 1010 at a focal plane of the objective 1006, is collimated into a beam of emission light by the objective 1006, reflected off a mirror 1012 toward a system of telescoping lenses 1014a, 1014b. As with adaptive optics used in point-scanning microscopy, described above, a wavefront modulating element 1018 that is optically conjugated to the rear pupil of the objective serves as both the wavefront sensor and the phase control device to modify individual beamlets of the beam of emission light. In other implementations, the single WME 1018 shown in FIG. 10 can be replaced with multiple active elements, similar to the techniques described above. Emission light modulated by the WME 1018 is directed toward a detector 1020 (e.g., a CCD detector), which images the emission light. In other implementations, the fast detector 1020 (e.g., a photomultiplier tube) can record the overall intensity of the signal of the emission light received by the detector, rather than recording an image of the sample. In some implementations, the system 1000 can include a field stop 1016 (e.g., a pinhole in an opaque mask) located at a plane conjugate to the image plane of the objective lens 1008, through which emission light passes, such that the field stop 1016 can discriminate light emitted from the focal plane of the objective lens 1006 from light emitted from other planes within the sample 1010.

Individual beamlets of the beam of emission light can be individually controlled (both the directions and phases with which they are reflected from the WME 1018) and the overall intensity of the resulting image recorded by detector 1020 can be monitored. Based on the monitored intensity, the angles and phase of the individual beamlets can be adjusted to create an image whose resolution is close to the diffraction limit, and in any case is closer to the diffraction limit than without the adaptive optics techniques.

In one implementation, as shown in FIG. 11, a single Fresnel lens pattern can be applied to the WME 1018. The Fresnel lens pattern then focuses the emission beam onto the detector 1020 to form a single image of the sample 1010, as shown in FIG. 11B. Then, as shown in FIG. 11C, an array of Fresnel lenses can be applied to different subregions of the WME 1018 to segment the emission light wavefront into different individually controllable beamlets and to produce an array of images of the sample, as shown in FIG. 11D, at the image plane of the detector 1020. For a perfect plane wave emission wavefront, the array of images would fall on a perfect grid. However, the deviation of each individual image from its ideal grid location can be used to measure the slope of the portion of the wavefront (and the angle of the beamlet that corresponds to that portion of the wavefront) used to create the individual image. Thus, measurement of the deviation of each individual image from its ideal grid location can be used to determine an array of wavefront slope measurements across the rear pupil of the objective 1006, from which the desired corrective wavefront can be reconstructed. Applying this correction to the WME 1018 and overlapping it with a single Fresnel lens pattern shown in FIG. 11A, which is used to focus the overall image onto the detector then recovers a diffraction-limited image of the sample 1010 at the detector 1020. In some implementation, e.g., when Fresnel lens patterns are not applied to the WME 1018, a focusing lens can be placed between the WME 1018 and the detector 1020 to focus the emission light onto the detector 1020.

As with two-photon fluorescence microscopy, if the sample 1010 does not exhibit field-position-dependent aberration, the resulting adaptive optics correction should recover diffraction-limited resolution everywhere in the field of view. If the aberration is field-dependent, an averaged correction over the entire field will be obtained, which should still improve signal and resolution. Furthermore, by analyzing the image shift using fluorescent features within different subfields of view, the field-dependent aberration can be measured, and a diffraction-limited image can be reconstructed by applying appropriate aberration patterns to each subfield of view sequentially.

Figure 12:
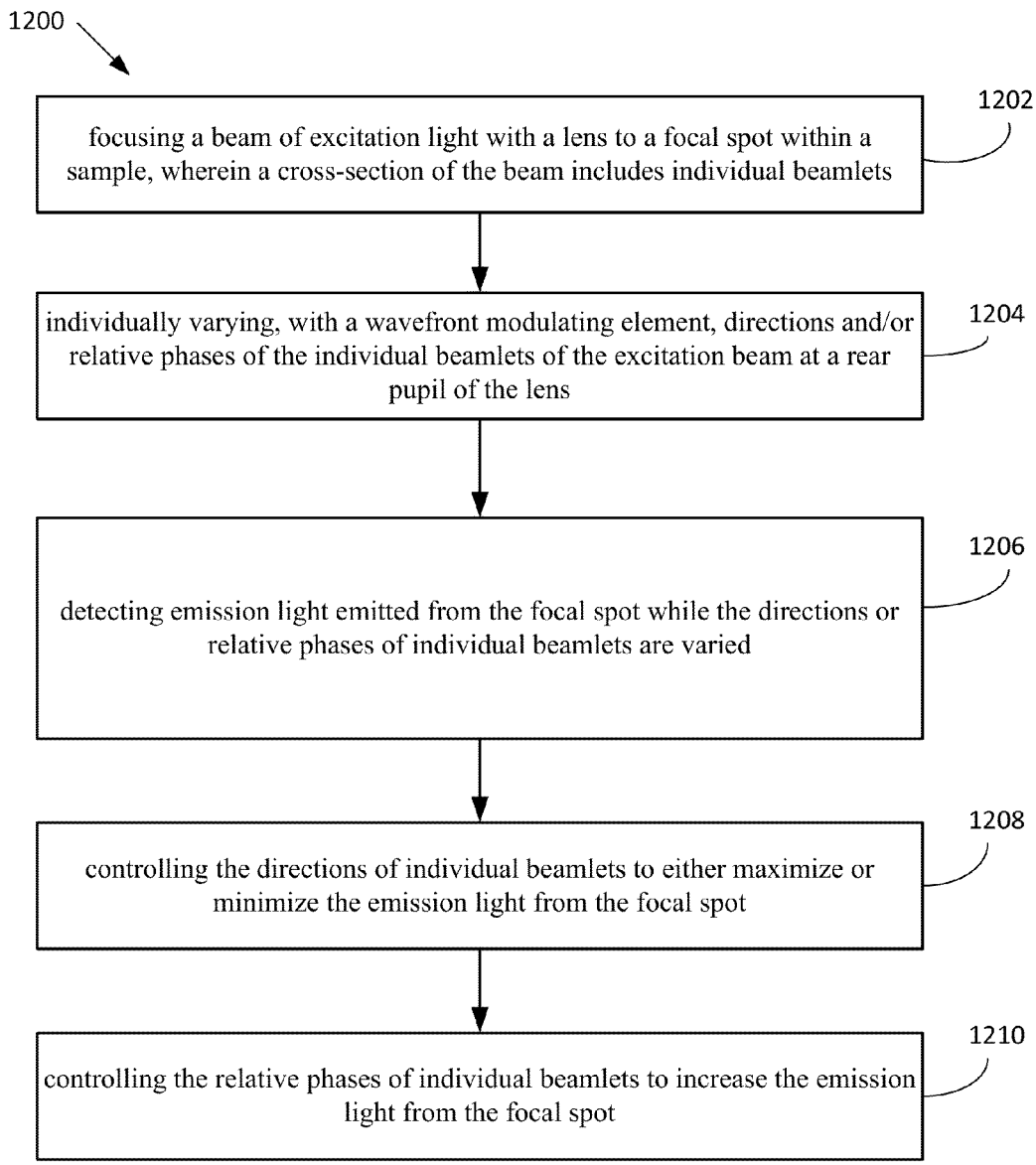
FIG. 12 is a flowchart of a process of focusing light in a sample.

FIG. 12 is a flowchart of a process 1200 of manipulating a focused light beam. In the process 1200, a beam of excitation light is focused with an objective lens to a focal spot within the sample, where a cross-section of the beam includes individual beamlets (1202). The focal spot is scanned to a plurality of different positions within the sample (1204). Emission light emitted from the focal spot when the focal spot is at the different positions is detected (1208), and an image of the sample is generated based on the detected emission light from the different positions of the focal spot (1210).

When the focal spot is at the different positions, the individual beamlets of the excitation beam are modulated with a wavefront modulating element to individually control directions and relative phrases of the individual beamlets at a rear pupil of the objective lens, where the directions of the individual beamlets are controlled to reduce a spatial extent of the focal spot, and the relative phases are controlled to increase an intensity of the excitation beam at the focal spot (1210).

Implementations of the various techniques described herein may be implemented in digital electronic circuitry, or in computer hardware, firmware, software, or in combinations of them. Implementations may implemented as a computer program product, i.e., a computer program tangibly embodied in an information carrier, e.g., in a machine-readable storage device or in a propagated signal, for execution by, or to control the operation of, data processing apparatus, e.g., a programmable processor, a computer, or multiple computers. A computer program, such as the computer program(s) described above, can be written in any form of programming language, including compiled or interpreted languages, and can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps may be performed by one or more programmable processors executing a computer program to perform functions by operating on input data and generating output. Method steps also may be performed by, and an apparatus may be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. Elements of a computer may include at least one processor for executing instructions and one or more memory devices for storing instructions and data. Generally, a computer also may include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory may be supplemented by, or incorporated in special purpose logic circuitry.

To provide for interaction with a user, implementations may be implemented on a computer having a display device, e.g., a cathode ray tube (CRT) or liquid crystal display (LCD) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

While certain features of the described implementations have been illustrated as described herein, many modifications, substitutions, changes and equivalents will now occur to those skilled in the art. It is, therefore, to be understood that the appended claims are intended to cover all such modifications and changes as fall within the true spirit of the embodiments.

What is claimed is:

1. A method of manipulating a focused light beam, the method comprising:
  focusing a beam of excitation light with a lens to a focal spot within a sample, wherein a cross-section of the beam includes individual beamlets;
  individually varying, with a wavefront modulating element, directions and/or relative phases of the individual beamlets of the excitation beam at a rear pupil of the lens;
  detecting emission light emitted from the focal spot while the directions or relative phases of individual beamlets are varied;

controlling the directions of individual beamlets to either maximize or minimize the emission light from the focal spot; and controlling the relative phases of individual beamlets to increase the emission light from the focal spot.

2. The method of claim 1, further comprising:

changing a location of the focal spot to a plurality of different positions within the sample;

detecting emission light from the plurality of different positions of the focal spot; and generating an image of the sample based on the detected emission light from the different positions of the focal spot.

3. The method of claim 2, further comprising, when the focal spot is at the different positions:

individually varying, with the wavefront modulating element, directions or relative phases of the individual beamlets of the excitation beam at the rear pupil of the lens;

detecting emission light emitted from the focal spot while the directions or relative phases of individual beamlets are varied; and controlling the directions of individual beamlets to either maximize or minimize the emission light from the focal spot; and controlling the relative phases of individual beamlets to increase the emission light from the focal spot.

4. The method of claim 1, wherein the excitation light has a first wavelength and the emission light has a second wavelength that is less than the first wavelength.

5. The method of claim 1, wherein the excitation light has a first wavelength and the emission light has a second wavelength that is greater than the first wavelength.

6. The method of claim 1, wherein the wavefront modulating element includes a reflective spatial light modulator and further comprising applying a global phrase ramp to light reflected from an active layer of the spatial light modulator to induce a non-zero direction between light reflected from the active layer and light reflected from other interfaces of the spatial light modulator.

7. The method of claim 1, further comprising determining the directions of individual beamlets used to maximize or minimize the emission light from the focal spot, wherein the determining includes, for at least some of the individual beamlets:

varying the direction of the beamlet at the rear pupil of the lens while maintaining fixed directions of the other beamlets at the rear pupil of the lens;

monitoring signal emission from the focal spot while the direction of the beamlet is varied; and based on the monitored signal emission, determining the direction of the beamlet.

8. The method of claim 7, further comprising, for at least some of the individual beamlets:

varying the phase of the beamlet over at least two phase values and then, for each of the phase values:

varying the direction of the beamlet at the rear pupil of the lens while maintaining fixed directions of the other beamlets at the rear pupil of the lens;

monitoring signal emission from the focal spot while the direction of the beamlet is varied; and based on the monitored signal emission, determining the direction of the beamlet that maximizes or minimizes the emission light from the focal spot.

9. The method of claim 7, further comprising, iterating, at least twice, the process of, for the at least some individual beamlets:

varying the direction of the beamlet at the rear pupil of the lens while maintaining fixed directions of the other beamlets at the rear pupil of the lens;

monitoring signal emission from the focal spot while the direction of the beamlet is varied; and based on the monitored signal emission, determining the direction of the beamlet that maximizes or minimizes the emission light from the focal spot.

10. The method of claim 7, further comprising determining the relative phases of individual beamlets, which increase the emission light from the focal spot, wherein the determining includes, for at least one of the individual beamlets:

varying the phase of the beamlet at the rear pupil of the lens while maintaining fixed phases of the other beamlets at the rear pupil of the lens;

monitoring signal emission from the focal spot while the phase of the beamlet is varied; and based on the monitored signal emission, determining the relative phase of the beamlet that increases the emission of signal light from the focal spot.

11. The method of claim 10, further comprising, iterating, at least twice, the process of, for the at least some individual beamlets:

varying the phase of the beamlet at the rear pupil of the lens while maintaining fixed phases of the other beamlets at the rear pupil of the lens;

monitoring signal emission from the focal spot while the phase of the beamlet is varied; and based on the monitored signal emission, determining the relative phase of the beamlet that increases the emission of signal light from the focal spot.

12. The method of claim 1, further comprising determining the directions of individual beamlets that maximize or minimize the emission light from the focal spot, wherein the determining includes, for at least one of the individual beamlets:

varying the direction of the beamlet at the rear pupil of the lens while maintaining fixed directions of the other beamlets at the rear pupil of the lens;

dithering an optical property of the varied beamlet at a dither frequency;

monitoring a spectral component of the signal emission from the focal spot substantially at the dither frequency while the direction of the beamlet is varied; and based on the monitored signal emission as a function of the direction of the beamlet, determining the direction of the beamlet that maximize or minimize the emission light from the focal spot.

13. The method of claim 1, further comprising determining the directions of individual beamlets that maximize or minimize the emission light from the focal spot, wherein the determining includes, for at least some of the individual beamlets:

simultaneously varying the directions of a first beamlet and a second beamlet at the rear pupil of the lens;

dithering an optical property of the first beamlet at a first dither frequency;

dithering an optical property of the second beamlet at a second dither frequency;

simultaneously monitoring spectral components of the signal emission emitted from the focal spot at the first and second dither frequencies associated with the first and second beamlets while the directions of the first and second beamlets are varied; and based on the monitored signal emission associated with each beamlet, determining the directions of the first and second beamlets that maximize or minimize the emission light from the focal spot.

14. The method of claim 13, wherein the first and second dither frequencies are uncorrelated.

15. The method of claim 1, wherein the cross-section of the beam includes at least N individual beamlets, with N>2, that are focused to the focal spot, and further comprising determining the directions of individual beamlets that maximize or minimize the emission light from the focal spot, wherein the determining includes:
   providing the N beamlets to the rear pupil of the lens;
   focusing the provided N beamlets to a focal spot in the sample; and
   for the provided N beamlets:
      simultaneously varying the directions of the N beamlets at the rear pupil of the lens;
      dithering an optical property of each of the N varied beamlet at a unique dither frequency;
      simultaneous monitoring spectral components of the signal emission emitted from the focal spot substantially at the N unique dither frequencies associated with the N beamlets while the directions of the N beamlets are varied; and
      based on the monitored signal emission associated with each of the N beamlets, determining the directions of the N beamlets.

16. The method of claim 15, wherein the directions of the N beamlets are varied by a first optical element and the optical properties of the N beamlets are dithered by a second optical element.

17. The method of claim 1, further comprising:
   focusing a reference beam to the focal spot to which the beam of excitation light is focused;
   determining the directions of individual beamlets that maximize or minimize the emission light from the focal spot, wherein the determining includes, for at least some of the individual beamlets:
   varying the direction of a beamlet at the rear pupil of the lens;
   diverting one or more of the individual beamlets, other than the beamlet that is varied, away from the rear pupil of the lens;
   monitoring signal emission from the focal spot while the direction of the beamlet is varied and while the one or more individual beamlets, other than the beamlet that is varied, is/are diverted away from the rear pupil of the lens; and
   based on the monitored signal emission, determining the direction of the beamlet that maximizes or minimizes the emission light from the focal spot.

18. The method of claim 17,
   wherein varying the direction of a beamlet at the rear pupil of the lens includes varying a position of a mirror from which the beamlet is reflected, and
   wherein diverting the one or more individual beamlets, other than the beamlet that is varied, includes selecting directions with which diverted beamlets are reflected from individual micromirrors in a digital micromirror array.

19. The method of claim 17,
   wherein varying the direction of a beamlet at the rear pupil of the lens includes varying an angle of a mirror from which the beamlet is reflected, and
   wherein diverting the one or more individual beamlets, other than the beamlet that is varied, includes selecting one or more phase ramps at positions on a spatial light modulator corresponding to the one or more individual beamlets to divert the one or more individual beamlets.

20. The method of claim 17,
   wherein varying the direction of a beamlet at the rear pupil of the lens includes varying an angle of a mirror from which the beamlet is reflected, and
   wherein diverting the one or more individual beamlets, other than the beamlet that is varied, includes selecting directions with which diverted beamlets are reflected from individual sections of a deformable mirror.

21. The method of claim 1,
   wherein P, where P is an integer, individual beamlets whose direction and/or relative phases are varied have cross-sections that overlap with each other at the rear pupil of the lens,
   and wherein controlling the directions and relative phases of the P individual beamlets includes independently controlling the directions of Q different beamlets at the rear pupil of the lens, where Q is an integer and Q>P.

22. The method of claim 1, further comprising:
   for each of a plurality of tip angles and for each of a plurality of tilt angles of an individual beamlet, changing a location of the focal spot to a plurality of different positions within the sample;
   for each of the plurality of tip angles and for each of the plurality of tilt angles and for each of the plurality of different positions of the focal spot within the sample detecting emission light detecting emission light emitted from the focal spot; and
   based on the emission light detected from the plurality of focal spot positions for each of the plurality of tip and tilt angles, determining the tip and tilt angles for a beamlet that maximize the emission light from the sample when integrated over all the positions of the focal spot.

23. The method of claim 1, where one or more beamlets in the cross-section of the beam are not focused to the focal spot.

24. A method for increasing the intensity of light at a focal spot on an image plane of an optical system, the method comprising:
   collecting a beam of emission light from a sample with a lens of the optical system, wherein a cross-section of a beam of the emission light emerging from a rear-pupil of the includes individual beamlets;
   focusing the light beam to the focal spot on the image plane;
   individually varying, with a wavefront modulating element, directions and/or relative phases of the individual beamlets of the emission light beam at the focal point;
   detecting the intensity of the light at the focal spot while the directions or relative phases of individual beamlets are varied; and
   controlling the directions and relative phases of individual beamlets to increase the intensity of the light at the focal spot.

25. The method of claim 24, where the focal spot is located at a pinhole in an opaque mask.

26. The method of claim 24, wherein the wavefront modulating element includes a reflective spatial light modulator and further comprising applying a global phrase ramp to light reflected from an active layer of the spatial light modulator to induce a non-zero direction between light reflected from the active layer and light reflected from other interfaces of the spatial light modulator.

27. The method of claim 24, further comprising determining the directions of individual beamlets used to increase the intensity of the light at the focal spot, wherein the determining includes, for at least some of the individual beamlets:

varying the direction of the beamlet at the focal spot while maintaining fixed directions of the other beamlets at the focal spot;

monitoring the intensity of the light at the focal spot while the direction of the beamlet is varied; and based on the monitored intensity, determining the direction of the beamlet.

28. The method of claim 27, further comprising, for at least some of the individual beamlets:

varying the phase of the beamlet over at least two phase values and then, for each of the phase values:

varying the direction of the beamlet at the focal spot while maintaining fixed directions of the other beamlets at the focal spot;

monitoring the intensity of the light at the focal spot while the direction of the beamlet is varied; and based on the monitored intensity, determining the direction of the beamlet.

29. The method of claim 27, further comprising, iterating, at least twice, the process of, for the at least some individual beamlets:

varying the direction of the beamlet at the focal spot while maintaining fixed directions of the other beamlets at the focal spot;

monitoring the intensity of the light at the focal spot while the direction of the beamlet is varied; and based on the monitored intensity, determining the direction of the beamlet.

30. The method of claim 27, further comprising determining the relative phases of individual beamlets that increase the intensity of the light at the focal spot, wherein the determining includes, for at least one of the individual beamlets:

varying the phase of the beamlet at the focal spot while maintaining fixed phases of the other beamlets at the focal spot;

monitoring the intensity of the light at the focal spot while the phase of the beamlet is varied; and based on the monitored intensity, determining the relative phase of the beamlet.

31. The method of claim 24, further comprising determining the directions of individual beamlets that increase the intensity of the light at the focal spot, wherein the determining includes, for at least one of the individual beamlets:

varying the direction of the beamlet at the focal spot while maintaining fixed directions of the other beamlets at the spot;

dithering an optical property of the beamlet at a dither frequency;

monitoring a spectral component of the intensity signal from the focal spot substantially at the dither frequency while the direction of the beamlet is varied; and based on the monitored spectral component of the intensity signal as a function of the direction of the beamlet, determining the direction of the beamlet.

32. The method of claim 24, further comprising determining the directions of individual beamlets that increase the intensity of the light at the focal spot, wherein the determining includes, for at least some of the individual beamlets:

simultaneously varying the directions of a first beamlet and a second beamlet at the focal spot;

dithering an optical property of a first beamlet at a first dither frequency;

dithering an optical property of a second beamlet at a second dither frequency;

simultaneously monitoring spectral components of the intensity signal from the focal spot substantially at the first and second dither frequencies associated with the first and second beamlets while the directions of the first and second beamlets are varied; and based on the monitored spectral components of the intensity signal emission associated with each beamlet, determining the directions of the first and second beamlets.

33. The method of claim 32, wherein the first and second dither frequencies are uncorrelated.

34. The method of claim 24, wherein the cross-section of the beam includes at least N individual beamlets, with N>2, that are focused to the focal spot, and further comprising determining the directions of individual beamlets that increase the intensity of the light at the focal spot, wherein the determining includes, for the N beamlets:

simultaneously varying the directions of the N beamlets at the focal spot;

dithering an optical property of each of the N beamlet at a unique dither frequency;

simultaneously monitoring spectral components of the intensity signal from the focal spot substantially at the N unique dither frequencies associated with the N beamlets while the directions of the N beamlets are varied; and based on the monitored spectral components of the intensity signal associated with each of the N beamlets, determining the directions of the N beamlets.

35. The method of claim 34, wherein the directions of the N beamlets are varied by a first optical element and the optical properties of the N beamlets are dithered by a second optical element.

36. A microscopy system comprising:

a light source configured to generate beam of excitation light, wherein a cross-section of the beam includes individual beamlets;

a lens configured to focus the beam of excitation light a focal spot within a sample;

a wavefront modulating element configured to individually vary directions or relative phases of the individual beamlets of the excitation beam at a rear pupil of the lens;

a detector configured to detect emission light emitted from the focal spot while the directions or relative phases of individual beamlets are varied; and wherein the wavefront modulating element is further configured to, in response to the detected emission light, control the directions of individual beamlets to either maximize or minimize the emission light from the focal spot and to control the relative phases of individual beamlets to increase the emission light from the focal spot.

37. The system of claim 36, further comprising:

one or more adjustable mirrors configured to change a location of the focal spot to a plurality of different positions within the sample, wherein, when the focal spot is at the different positions, the wavefront modulating element is configured to individually vary directions or relative phases of the individual beamlets of the excitation beam at a rear pupil of the lens and to, in response to the detected emission light, control the directions of individual beamlets to either maximize or minimize the emission light from the focal spot and to control the relative phases of individual beamlets to increase the emission light from the focal spot; and a processor configured to generate an image of the sample based on the detected emission light from the different positions of the focal spot.

38. The system of claim 36, wherein the excitation light has a first wavelength and the emission light has a second wavelength that is less than the first wavelength.

39. The system of claim 36, wherein the excitation light has a first wavelength and the emission light has a second wavelength that is great than the first wavelength.

40. The system of claim 36, wherein the wavefront modulating element includes a reflective spatial light modulator that is configured to apply a global phrase ramp to light reflected from an active layer of the spatial light modulator to induce a non-zero angle between light reflected from a front surface of the spatial light modulator and light reflected from the active layer.

41. The system of claim 36, wherein the wavefront modulating element is further configured to vary the direction of at least one of the individual beamlet at the rear pupil of the lens while maintaining fixed directions of the other beamlets at the rear pupil of the lens, and further comprising:
   one or more processors configured for determining the directions of the at least one individual beamlet that maximizes or minimizes the emission light from the focal spot based on the detected emission light that is emitted from the sample while the direction of the beamlet at the rear pupil of the lens is varied and the directions of the other beamlets at the rear pupil of the lens are maintained in fixed directions.

42. The system of claim 41, wherein the wavefront modulating element is further configured to vary the phase of an individual beamlet over at least two phase values and then, for each of the phase values to vary the direction of the beamlet at the rear pupil of the lens while maintaining fixed directions of the other beamlets at the rear pupil of the lens, and further comprising:
   one or more processors configured for determining the directions of individual beamlets that maximize or minimize the emission light from the focal spot based on the detected emission light that is emitted from the sample while the direction of the beamlet at the rear pupil of the lens is varied for each of the phase values.

43. The system of claim 41, wherein the wavefront modulating element is further configured to vary the phase of an individual beamlet at the rear pupil of the lens while maintaining fixed phases of the other beamlets at the rear pupil of the lens, and further comprising:
   one or more processors configured to, based on the detected emission light that is emitted from the sample while the phase of the beamlet is varied, determine the relative phase of the beamlet that increases the emission of signal light from the focal spot.

44. The system of claim 41,
wherein the light source provides P individual beamlets whose directions and/or relative phases are varied and having cross-sections that overlap with each other at the rear pupil of the lens, where P is an integer,
and wherein the wavefront modulating element is configured to control the directions and relative phases of the P individual beamlets includes independently controlling the directions of Q different beamlets at the rear pupil of the lens, where Q is an integer and Q>P.

45. The system of claim 36,
wherein the wavefront modulating element is further configured to, for at least one of the individual beamlets, vary the direction of the beamlet at the rear pupil of the lens while maintaining fixed directions of the other beamlets at the rear pupil of the lens, and to dither an optical property of the at least one individual beamlet at a dither frequency,
wherein the detector is further configured to detect a spectral component of the emission light substantially at the dither frequency while the direction of the beamlet is varied, and further comprising:
   one or more processors configured to, based on the detected spectral component of the emission light as a function of the direction of the varied beamlet, determine the direction of the at least one individual beamlet that maximizes or minimizes the emission light from the focal spot.

46. The system of claim 36,
wherein the wavefront modulating element is further configured to, for at least one of the individual beamlets, vary the direction of the beamlet at the rear pupil of the lens while maintaining fixed directions of the other beamlets at the rear pupil of the lens, and further comprising:
   a dithering optical element configured to dither an optical property of the at least one individual beamlet at a dither frequency, wherein the detector is further configured to detect a spectral component of the emission light at the dither frequency while the direction of the beamlet is varied; and
   one or more processors configured to, based on the detected spectral component of the emission light as a function of the direction of the varied beamlet, determine the direction of the at least one individual beamlet that maximizes or minimizes the emission light from the focal spot.

47. The system of claim 46, wherein the wavefront modulating element includes a reflective spatial light modulator and wherein the dithering optical element includes a digital micro-mirror array or a deformable mirror.

48. The system of claim 36, wherein the wavefront modulating element is further configured to, for at some of the individual beamlets, simultaneously vary the directions of the individual beamlets at the rear pupil of the lens while maintaining fixed directions of the other beamlets at the rear pupil of the lens, and further comprising:
   a dithering optical element configured to dither an optical property of the at least one individual beamlet at a dither frequency, wherein the detector is further configured to detect a spectral component of the emission light at the dither frequency while the direction of the beamlet is varied; and
   one or more processors configured to, based on the detected spectral component of the emission light as a function of the direction of the varied beamlet, determine the direction of the at least one individual beamlet that maximizes or minimizes the emission light from the focal spot.

49. The system of claim 36, wherein the wavefront modulating element is further configured to, for at some of the individual beamlets, simultaneously vary the directions of the individual beamlets at the rear pupil of the lens while maintaining fixed directions of the other beamlets at the rear pupil of the lens, and further comprising:
   a dithering optical element configured to dither an optical property of a first beamlet at a first dither frequency and to dither an optical property of a second beamlet at a second dither frequency while its direction is varied, wherein the detector is further configured to detect spectral components of the emission light substantially at the first and second dither frequencies while the direction of the beamlets are varied; and
   one or more processors configured to, based on the detected spectral components of the emission light as a function of the directions of the varied beamlets, determine the direction of first and second individual beamlet that maximizes or minimizes the emission light from the focal spot.

50. The system of claim 49, wherein the first and second dither frequencies are uncorrelated.

51. The system of claim 49, wherein the wavefront modulating element is different from the dithering optical element.

52. The system of claim 36,
wherein the cross-section of the beam includes at least N individual beamlets, with N>2,
wherein the lens is configured to focus the N individual beamlets to the focal spot,
wherein the wavefront modulating element is configured to simultaneously vary the directions of the N beamlets at the rear pupil of the lens, and further comprising:
a dithering optical element configured to dither an optical property of the N individual beamlets at unique dither frequencies while the directions of the beamlets are varied, wherein the detector is further configured to detect spectral components of the emission light substantially at the N dither frequencies while the direction of the beamlets are varied; and
one or more processors configured to, based on the detected spectral components of the emission light as a function of the directions of the varied beamlets, determine the direction of N individual beamlet that maximize or minimize the emission light from the focal spot.

53. The system of claim 52, wherein the wavefront modulating element is different from the dithering optical element.

54. The system of claim 36, wherein the wavefront modulating element is configured to vary the direction of an individual beamlet at the rear pupil of the lens, and further comprising:
one or more reference beam optical elements configured for providing a reference beam to the focal spot to which the beam of excitation light is focused;
a diverting optical element configured to divert one or more of the individual beamlets, other than the beamlet that is varied, away from the rear pupil of the lens, wherein the detector is further configured to monitor signal emission from the focal spot while the direction of the beamlet is varied and while the one or more individual beamlets, other than the beamlet that is varied, is/are diverted away from the rear pupil of the lens; and
one or more processors configured to, based on the monitored signal emission, determining the direction of the beamlet that maximizes or minimizes the emission light from the focal spot.

55. The system of claim 54,
wherein the diverting optical element includes digital micromirror array configured to selectively divert individual beamlets away from the rear pupil of the lens, and wherein varying the direction of a beamlet at the rear pupil of the lens includes varying a position of one or more mirrors of the array from which the beamlet is reflected.

56. The system of claim 54,
wherein the diverting optical element is the spatial light modulator, wherein the spatial light modulator is configured to apply one or more phase ramps on the spatial light modulator corresponding to one or more individual beamlets to be diverted, and
further comprising one or more mirrors configured to vary the direction of the varied beamlet at the rear pupil of the lens.

57. The system of claim 54,
wherein the diverting optical element includes a deformable mirror, wherein the deformable mirror is configured to change its shape to cause one or more individual beamlets to be diverted, and
further comprising one or more mirrors configured to vary the direction of the varied beamlet at the rear pupil of the lens.

58. The system of claim 36, wherein the wavefront modulating element includes a reflective spatial light modulator.

59. The system of claim 36, wherein the wavefront modulating element includes a deformable mirror.

60. The system of claim 36, wherein the wavefront modulating element includes a digital micro-mirror array.

61. A microscopy system comprising:
a lens configured for collecting a beam of emission light from a sample, wherein the beam includes individual beamlets;
one or more focusing optical elements configured to focus the emission light beam to the focal spot;
a wavefront modulation element configured to individually vary directions and/or relative phases of the individual beamlets of the emission light beam at the focal spot;
a detector configured to detect an intensity of the light at the focal spot while the directions or relative phases of individual beamlets are varied; and
wherein the wavefront modulating element is further configured to, in response to the detected emission light, control the directions and relative phases of individual beamlets to increase the intensity of the light at the focal spot.

62. The system of claim 61, further comprising an opaque mask defining a pinhole, wherein the pinhole is located at the focal spot.

63. The system of claim 61, wherein the wavefront modulating element includes a reflective spatial light modulator configured to apply a global phrase ramp to light reflected from an active layer of the spatial light modulator to induce a non-zero direction between light reflected from the active layer and light reflected from other interfaces of the spatial light modulator.

64. The system of claim 61,
wherein the wavefront modulating element is further configured to vary the direction of the beamlet at the focal spot while maintaining fixed directions of the other beamlets at the focal spot;
wherein the detector is configure to monitor the intensity of the light at the focal spot while the direction of the beamlet is varied, and further comprising:
one or more processors configured for determining, based on the monitored intensity, the directions of individual beamlets used to increase the intensity of the light at the focal spot.

65. The system of claim 64,
wherein the wavefront modulating element is further configured to vary the phase of the beamlet over at least two phase values and then, for each of the phase values, to vary the direction of the beamlet at the focal spot while maintaining fixed directions of the other beamlets at the focal spot;
wherein the detector is configured to monitor the intensity of the light at the focal spot while the direction of the beamlet is varied, and further comprising:
one or more processors configured for determining, based on the monitored intensity, the direction of the beamlet.

66. The system of claim 64,
   wherein the wavefront modulating element is configured to vary the phase of the beamlet at the focal spot while maintaining fixed phases of the other beamlets at the focal spot;
   wherein the detector is configured to monitor the intensity of the light at the focal spot while the phase of the beamlet is varied, and further comprising
   one or more processors configured to determine, based on the monitored intensity, the relative phase of the beamlet that increases the intensity of the light at the focal spot.

67. The system of claim 61, wherein the wavefront modulating element is configured to vary the direction of the beamlet at the focal spot while maintaining fixed directions of the other beamlets at the spot, and further comprising:
   a dithering optical element configured to dither an optical property of the beamlet at a dither frequency, and wherein the detector is configured to monitor a spectral component of the intensity signal at the focal spot substantially at the dither frequency while the direction of the beamlet is varied; and
   one or more processors configured to determine the direction of the beamlet based on the monitored spectral component of the intensity signal as a function of the direction of the beamlet.

68. The system of claim 67, wherein the first and second dither frequencies are uncorrelated.

69. The system of claim 61, wherein the cross-section of the emission beam includes at least N individual beamlets, with N>1, that are focused to the focal spot,
   wherein the wavefront modulating element is configured to simultaneously vary the directions of the N beamlets at the focal spot; and further comprising:
   a dithering optical element configured to dither an optical property of each of the N beamlets at a unique dither frequency, and wherein the detector is configured to monitor spectral components of the intensity signal from the focal spot substantially at the N unique dither frequencies associated with the N beamlets while the directions of the N beamlets are varied; and
   one or more processors configured to determine, based on the monitored spectral components of the intensity signal associated with each of the N beamlets, the directions of the N beamlets that increase the intensity of the light at the focal spot.

* * * * *